US008021831B2

(12) United States Patent
Ueno et al.

(10) Patent No.: US 8,021,831 B2
(45) Date of Patent: Sep. 20, 2011

(54) TAXANE CHEMOSENSITIVITY PREDICTION TEST

(75) Inventors: Naoto T. Ueno, Houston, TX (US); Hideki Ishihara, Hyogo (JP); Tamotsu Sudo, Kobe (JP); Tomoko Matsushima, Kobe (JP)

(73) Assignees: Board of Regents, The University of Texas System, Austin, TX (US); Sysmex Corporation, Kobe (JP)

( * ) Notice: Subject to any disclaimer, the term of this patent is extended or adjusted under 35 U.S.C. 154(b) by 480 days.

(21) Appl. No.: 10/926,409

(22) Filed: Aug. 25, 2004

(65) Prior Publication Data
US 2005/0131057 A1 Jun. 16, 2005

Related U.S. Application Data

(60) Provisional application No. 60/497,665, filed on Aug. 25, 2003.

(51) Int. Cl.
*C12Q 1/00* (2006.01)
*C12Q 1/68* (2006.01)
*G01N 33/53* (2006.01)
*G01N 33/567* (2006.01)
*G01N 33/574* (2006.01)

(52) U.S. Cl. ............ 435/4; 435/6; 435/7.1; 435/7.21; 435/7.23

(58) Field of Classification Search .................. None
See application file for complete search history.

(56) References Cited

U.S. PATENT DOCUMENTS

| 5,834,298 A | 11/1998 | Benezra ................ 435/254.21 |
| 2002/0006613 A1 | 1/2002 | Shyjan et al. .................. 435/6 |

FOREIGN PATENT DOCUMENTS

| GB | 2 335 739 | | 9/1999 |
| JP | 2002-503822 | | 2/2002 |
| WO | WO99/42834 | * | 8/1999 |

OTHER PUBLICATIONS

Ibrado et al. (Leukemia 1998; 12: 1930-1936).*
Shah et al. (Clinical Cancer Research 2001; 7: 2168-2181).*
Stumm et al. (Oncology 2004; 66: 101-111).*
Duan et al. (Clinical Cancer Research 1999; 5: 3445-3453).*
Duan et al. (Cancer Chemotherapy Pharmacology 2005; 55: 277-285).*
Freshney (Culture of Animal Cells, A Manual of Basic Technique, Alan R. Liss, Inc., 1983, New York, p. 4).*
Dermer (Bio/Technology, 1994, 12:320).*
Cailleau et al. (In Vitro 1978 14: 911-915).*
NCBI/MESH (CDC2 Protein Kinase 1991).*
Moos et al. (Cell Growth and Differentiation, 1998 9:687-697).*
Choy, H. (Crit. Rev. Oncol./Hem. 2001 37:237-247).*
Chen et al. (Cellular Pharmacology 1995; 2: 249-257).*
Granziero et al. (Eur. J. Immunol. 1999, 29:1127-1138).*
Byers, T. (CA Journal, vol. 49, No. 6, Nov./Dec. 1999).*
Tockman (Cancer Res., 1992, 52:2711s-2718s).*
Slamon et al. (Science vol. 235, Jan. 1987, pp. 177-182).*
ATCC®, 1975.*
Duan et al. (Clinical Cancer Research 1999, 5: 3445-3453).*
Taxol® Label (New Dosage Regimen, Jun. 20, 2000).*
Vanhoefer et al. (Annals of Oncology 1997; 8: 1221-1228).*
Shannon et al. (Molecular Biology of the Cell 2002; 13: 3706-3719).*
Chadebech et al., "Up-regulation of cdc2 protein during paclitaxel-induced apoptosis," *Int. J. Cancer*, 87:779-786, 2000.
Goncalves et al., "Resistance to taxol in lung cancer cells associated with increased microtubule dynamics," *PNAS*, 98:11737-11741, 2001.
Lanzi et al., "Cell cycle checkpoint efficiency and cellular reponse to paclitaxel in prostate cancer cells," *The Prostate*, 48:254-264, 2001.
Michalides et al., "Overexpression of cyclin D1 enhances taxol induced mitotic death in MCF7 cells," *Breast Cancer Research and Treatment*, 84:55-63, 2002.
Wang et al., "Paclitaxel-induced cell death," *Cancer*, 88:2619-2628, 2000.
Wang et al., "Significance of MAD2 expression to mitotic checkpoint control in ovarian cancer cells," *Cancer Research*, 62:1662-1668, 2002.
Yoshizaki et al., "Unscheduled expression of cyclins by anti-cancer drug exposure," *Human Cell.*, 11:27-34, 1998.
Giannakakou et al., "Paclitaxel-resistant human ovarian cancer cells have mutant beta-tubulins that exhibit impaired paclitaxel-driven polymerization," *J. Biol. Chem.*, 272(27):17118-17125, 1997.
Huang et al., "Inhibitory effects of topical application of low doses of curcumin on 12-O-tetradecanoylphorbol-13-acetate-induced tumor promotion and oxidized DNA bases in mouse epidermis," *Carcinogenesis*, 18:83-88, 1997.
Huang et al., "Activation of MAD 2 checkprotein and persistence of cyclin B1/CDC 2 activity associate with paclitaxel-induced apoptosis in human nasopharyngeal carcinoma cells," *Apoptosis*, 5(3):235-241, 2000.
Meikrantz and Schlegel, "Suppression of apoptosis by dominant negative mutants of cyclin-dependent protein kinases," *J. Biol. Chem.*, 271(17):10205-10209, 1996.

(Continued)

*Primary Examiner* — Peter J Reddig
(74) *Attorney, Agent, or Firm* — Fulbright & Jaworski LLP

(57) ABSTRACT

The present invention provides a method for determining the chemosensitivity of a cancer cell to a taxane comprising assessing the effect of the taxane on the expression level or activity of one or more cell cycle molecules in a cancer cell. Such a method makes use of an automated analyzer system wherein cell cycle parameters (molecules) such as CDK1 kinase activity, CDK1 expression, CDK2 kinase activity, CDK2 expression, MAD2 expression, Cyclin B1, Cyclin E expression, p21 expression, and CDK6 expression; are assessed. The present invention further provides a method of obtaining a cell cycle profile of a cancer cell that is sensitive to a taxane.

13 Claims, 14 Drawing Sheets

OTHER PUBLICATIONS

Nigg, "Mitotic kinases as regulators of cell division and its checkpoints," *Nat. Rev. Mol. Cell Biol.*, 2:21-32, 2001.

Shen et al., "Taxol-induced p34cdc2 kinase activation and apoptosis inhibited by 12-O-tetradecanoylphorbol-13-acetate in human breast MCF-7 carcinoma cells," *Cell Growth Differ.*, 9(1):23-29, 1998.

Sudo et al., "Dependence of paclitaxel sensitivity on a functional spindle assembly checkpoint," *Cancer Res.*, 64:2502-2508, 2004.

Tan et al., "Phosphorylation on tyrosine-15 of p34(Cdc2) by ErbB2 inhibits p34(Cdc2) activation and is involved in resistance to taxol-induced apoptosis," *Mol. Cell*, 9(5):993-1004, 2002.

Tang et al., "Photoaffinity labelling of cyclic GMP-inhibited phosphodiesterase (PDE III) in human and rat platelets and rat tissues: effects of phosphodiesterase inhibitors," *Eur J Pharmacol*, 268(1):105-114, 1994.

Yu et al., "Overexpression of ErbB2 blocks Taxol-induced apoptosis by upregulation of p21Cip1, which inhibits p34Cdc2 kinase," *Mol Cell*, 2:581-591, 1998.

Anand et al., "AURORA-A amplification overrides the mitotic spindle assembly checkpoint, inducing resistance to Taxol," *Cancer Cell*, vol. 3:51-62, 2003.

Japanese Office Action, issued in Japanese Application No. 2002-503822, mailing date on May 10, 2010 (English Translation).

Supplementary European Search Report, issued in European Application No. 04782204.4 - 2112, mailing date: Dec. 15, 2009.

Abal et al., "Taxanes: microtubule and centrosome targets, and cell cycle dependent mechanisms of action," *Current Cancer Drug Targets*, 3:193-203, 2003.

Anand et al., "AURORA-A amplification overrides the mitotic spindle assembly checkpoint, inducing resistance to Taxol," *Cancer Cell*, 3:51-62, 2003.

Hochhauser et al., "Effect of cyclin D1 overexpression on drug sensitivity in a human fibrosarcoma cell line," *Journal of the National Cancer Institute*, 88:1269-1275, 1996.

Lee et al., "Inactivation of the mitotic checkpoint as a determinant of the efficacy of microtubule-targeted drugs in killing human cancer cells," *Molecular Cancer Therapeutics*, 3:661-669, 2004.

Li et al., "Establishment, characterization and drug sensitivity of four new human soft tissue sarcoma cell lines," Database Medline—NLM8945624, 1996.

Rantanen et al., "Mutations of TP53 do not correlate with the sensitivity to paclitaxel—a study using 27 gynaecological cancer cell lines," *European Journal of Cancer*, 38:1783-1791, 2002.

Schmidt and Fan, "Protection against chemotherapy-induced cytotoxcity by cyclin-dependent kinase inhibitors (CKI) in CKI-responsive cells compared with CKI-unresponsive cells," *Oncogene*, 20:6164-6171, 2001.

Schmidt et al., "Differential modulation of paclitaxel-mediated apoptosis by $p21^{Waf1}$ and $p27^{Kip1}$," *Oncogene*, 19:2423-2429, 2000.

Smith and Seo, "Sensitivity of cyclin E-overexpressing cells to cisplatin/taxol combinations," *Anticancer Research*, 20:2537-2540, 2000.

Stewart et al., "Cell-cycle dysregulation and anticancer therapy," *TRENDS in Pharmacological Sciences*, 24:139-145, 2003.

Stewart et al., "Defective $G_1$-S cell cycle checkpoint function sensitizes cells to microtubule inhibitor-induced apoptosis," *Cancer Research*, 59:3831-3837, 1999.

Van Poznak et al., "Assessment of molecular markers of clinical sensitivity to single-agent taxane therapy for metastatic breast cancer," *Journal of Clinical Oncology*, 20:2319-2326, 2002.

* cited by examiner

TAXANE CHEMOSENSITIVITY PREDICTION TEST

This application claims the priority of U.S. Provisional Patent Application Ser. No. 60/497,665, filed Aug. 25, 2003, the entire disclosure of which is specifically incorporated herein by reference.

BACKGROUND OF THE INVENTION

1. Field of the Invention

The present invention relates generally to the fields of cancer therapy and cancer prevention. More particularly, it concerns predicting taxane chemosensitivity in a cancer patient.

2. Description of the Related Art

One of the main problems associated with cancer chemotherapy is that individual patients with the same histology do not respond identically to a given agent or a given therapeutic protocol. The response range may vary in large proportions, even in chemosensitive tumors, such as breast cancer. A number of determinants of drug sensitivity are well known, such as drug dose, drug combinations and schedule of administration, patient age and status, tumor localization, etc., but the intrinsic sensitivity of a given tumor is a major factor which remains difficult to evaluate. Numerous mechanisms of resistance have been identified and some of them can be evaluated on tumor biopsies, but they do not solve the problem of tumor sensitivity to anticancer drugs. This has lead to a number of research to try to individualize drug treatment as a function of the sensitivity of tumor cells.

One approach to determine the sensitivity of anticancer agents on tumor cells obtained from patients involves an in vitro test, the Human Tumor Stem Cell Assay (HTSCA). This assay along with a variety of other assays developed, all involve four basic steps: 1) isolation of cells; 2) incubation of cells with drugs; 3) assessment of cell survival; and 4) interpretation of the result, which are all used to predict how effective the drug may be in a patient. However, these in vitro assays are often a poor predictor of chemosensitivity to anticancer agents in vivo. Currently, the standard protocol for chemosensitivity prediction testing is performed by an ex vivo test. In this protocol, surgically resected tissue is embedded in medium containing an anti-cancer drug, and incubated for one week. The size or viability of tissue is then measured, and the sensitivity determined. However, this method is time-consuming, completely manual and expensive ($600-1000 for one test). Thus far, chemosensitivity testing has not reached clinical use, and, presently, no successful prediction of sensitivity of a tumor to an anticancer drug in a given patient can be achieved routinely.

One group of anticancer agents for which the chemosensitivity needs to be determined involves the taxanes, such as paclitaxel. It has been indicated in the literature that paclitaxel resistance might be related to the spindle assembly checkpoint and Cdk1. When paclitaxel stabilizes microtubules and interferes with the dynamic changes that occur during formation of the mitotic spindle, the spindle assembly checkpoint is activated to make cells arrest at mitosis (Horwitz et al., 1982). The mitotic checkpoint/spindle assembly checkpoint, also known as the cell cycle, monitors accurate chromosomal segregation and plays a crucial role in maintaining genome homeostasis. This checkpoint monitors both the attachment of chromosomes to the mitotic spindle and the tension across the sister chromatid generated by microtubules to prevent premature chromosomal segregation.

The molecular components of the spindle assembly checkpoint were initially identified in *Saccharomyces cerevisiae*. Mammalian homologues of the checkpoint proteins include Mad1, Mad2, BubR1, Bub3, and Mps1 (Li and Benezra, 1996; Jin et al., 1998; Taylor et al., 1998; Chan et al., 1999). The checkpoint machinery is a protein complex composed of Mad1, Mad2, BubR1, Bub3 and cdc20, located at the kinetocore of the chromosome. The target of this checkpoint is the anaphase-promoting complex (APC) and its co-activator Cdc20. Mad2 and BubR1 are located downstream and appear to be the major proteins of this machinery, interacting with Cdc20 directly and inhibiting APC activity cooperatively (Fang et al., 1998; Sudakin et al., 2001; Tang et al., 2001; Fang, 2002).

In tumor cells, defects in the checkpoint are often observed, and these are believed to induce genome instability. Recently, Huang et al. (2000) suggested that MAD2 and CDK1 kinase are cooperatively involved in Paclitaxel-induced apoptosis. In other reports, activation of CDK1 was shown to be required for apoptosis induction through caspase-3 activation (Tan et al., 2002), and p21Waf1, a CDK1 inhibitor at M-phase, was demonstrated to play a key role in the inhibition of Paclitaxel-induced apoptosis (Fang et al., 2000).

Cdk1, combined with mitotic cyclins, is a universal master kinase required for regulation of mitosis (Nigg, 2001). Cdk1 activity is maximized in accordance with activation of the spindle assembly checkpoint. Previous reports using either a Cdk inhibitor or dominant-negative Cdk1 have shown that Cdk1 is critical for paclitaxel-induced cell death inhibitor or dominant-negative Cdk (Meikrantz and Schlegel, 1996; Shen et al., 1998); however, whether activation of Cdk1 is the cause or the consequence of activated checkpoint activation remains unclear. The relationship between the spindle assembly checkpoint and paclitaxel sensitivity therefore, remains unclear.

Thus, new and better approaches to the use anticancer agents such as taxanes in the treatment of cancer are needed. The effectiveness of these agents may be determined by assessing the chemosensitivity.

SUMMARY OF THE INVENTION

A major problem of cancer therapy is the resistance of a cancer cell to a chemotherapeutic agent. The present invention therefore provides a method for determining taxane chemosensitivity of a cancer cell or tumor tissue. The method is effective for all anti-cancer drugs having a skeleton of taxane, such as paclitaxel and docetaxel.

Thus, in a particular embodiment, the present invention provides a method of determining the chemosensitivity of a cancer cell to a taxane comprising assessing the effect of the taxane on the expression level or activity of one or more cell cycle molecules in the cancer cell. The cancer cell as contemplated in the present invention may be obtained from a patient. In some embodiments of the invention, the cancer cell may be a tissue sample such as a biopsy tissue sample, an ex vivo cultivated biopsy tissue sample, a surgically-dissected tissue sample, or an ex vivo cultivated surgically-dissected tissue sample.

A cell-cycle molecule of the present invention may comprise one or more of cyclin dependent kinases (CDKs), cyclins, CDK inhibitors (CDKIs), p53 or mitotic/spindle assembly checkpoint molecules. In some embodiments the present invention comprises assessing 1, 2, 3, 4, 5, 6, 7, 8, 9, 10, 11, 12, 13, 14, 15, 16, 17, 18, 19, 20, or more cell cycle molecule(s). In particular embodiments, the invention comprises assessing one or more cell cycle molecule(s) for CDK activity such as CDK1 activity, CDK2 activity, CDK4 activity or CDK6 activity, but is not limited to such. In another particular embodiment, the present invention comprises assessing expression of one or more CDK molecules such as CDK1 expression, CDK2 expression, CDK4 expression or CDK6 expression. In yet another particular embodiment, the present invention comprises assessing the expression of one or more cyclin molecules such as cyclin B1 expression or cyclin E expression. In still yet another particular embodiment, the present invention comprises assessing the expression of one or more CDKIs such as but not limited to p16 expression, p21/Waf1 expression, or p27/Kip1 expression. In still yet a further particular embodiment, the present invention comprises assessing expression of one or more mitotic/spindle assembly checkpoint molecules such as but not limited to MAD2 expression or BubR1 expression.

In particular embodiments of the invention, any molecule or compound, or derivative or analogue thereof having a skeleton of taxane, such as paclitaxel and docetaxel is contemplated in the present invention.

A cancer cell as contemplated in the present invention may include but is not limited to a breast cancer cell, a prostate cancer cell, a skin cancer cell, lung cancer cell, head and neck cancer cell, bladder cancer cell, bone cancer cell, bone marrow cancer cell, brain cancer cell, colon cancer cell, esophageal cancer cell, gastrointestinal cancer cell, gum cancer cell, kidney cancer cell, liver cancer cell, nasopharynx cancer cell, ovarian cancer cell, stomach cancer cell, testis cancer cell, tongue cancer cell, or uterine cancer cell.

The cancer cell may be obtained from a patient or subject prior to administration of an anticancer therapy or after administration of an anticancer therapy. The anticancer therapy may be a chemotherapy or a radiotherapy but is not limited to such.

In particular embodiments, the present invention comprises obtaining a cell-cycle profile. A cell cycle profile as contemplated in the present invention comprises measuring, determining, assessing, or detecting the activity or expression of cell cycle molecules (e.g., proteins), in a cancer cell of a patient having a taxane therapy. By cell-cycle profiling, molecules that regulate sensitivity of a taxane may be analyzed. The activity or expression of the cell-cycle molecules may be measured, determined, assessed, or detected by methods known to those of skill in the art. In some embodiments, the cell-cycle profile may be obtained using an automated analyzer or device such as a cell cycle or multi-protein analyzer. It is contemplated that the cell-cycle profile may be compared with the cell-cycle profile of a cancer cell that is sensitive to a taxane. It is also contemplated that the cell-cycle profile may be compared with the cell-cycle profile of a cancer cell that is not sensitive to a taxane. The cell-cycle profile may be compared before administration of an anticancer therapy to that of the cell-cycle profile after administration of an anti-cancer therapy.

In some embodiments, obtaining a cell-cyle profile comprises measuring, determining, assessing, or detecting 1, 2, 3, 4, 5, 6, 7, 8, or 9 of the following parameters: (1) CDK1 kinase activity; (2) CDK1 expression (for calculation of CDK1 specific activity); (3) CDK2 kinase activity; (4) CDK2 expression (for calculation of CDK2 specific activity); (5) MAD2 expression; (6) Cyclin B1; (7) Cyclin E expression; (8) p21 expression; or (9) CDK6 expression. In some embodiments, a cell-cycle profile useful for differentiating taxane sensitive and taxane resistant cells comprises 1, 2, 3, 4, 5, 6, or 7 of the following parameters: (1) CDK1 specific activity 24 hr after taxane treatment; (2) CDK2 specific activity before taxane treatment; (3) MAD2 expression before taxane treatment; (4) Cyclin B1 before taxane treatment; (5) Cyclin E expression before taxane treatment; (6) p21 expression before taxane treatment; and (7) CDK6 expression before taxane treatment.

In still another embodiment, the present invention further comprises making a decision regarding the treatment of a patient having cancer. In still yet a further embodiment, the present invention comprises assessing the survival of the patient having the cancer.

In another particular embodiment, the present invention provides a method of treating or preventing cancer in a patient comprising: a) determining the effect of a taxane on the expression level or activity of one or more cell cycle molecules in a cancer cell of a patient; b) assessing the sensitivity of the cancer to the taxane; and c) administering a taxane to the patient. Assessing the sensitivity of the cancer to the taxane comprises obtaining a cell-cycle profile, which may be obtained using an automated analyzer.

A cancer such as, but not limited to, a breast cancer, a prostate cancer, a skin cancer, lung cancer, head and neck cancer, bladder cancer, bone cancer, bone marrow cancer, brain cancer, colon cancer, esophageal cancer, gastrointestinal cancer, gum cancer, kidney cancer, liver cancer, nasopharynx cancer, ovarian cancer, stomach cancer, testis cancer, tongue cancer, or uterine cancer is contemplated in the present invention.

The taxane, derivatives or analogs thereof, may be administered once or more than once intravenously, or intratumorally, but is not limited to such method of administration. The taxane of the present invention may further comprise administering an anticancer therapy such as a chemotherapy or radiotherapy. Such anticancer therapies may be administered prior to the taxane, after the taxane or at the same time as the taxane. The anticancer therapy may further be administered once or more than once to the subject or patient.

It is contemplated that any method or composition described herein can be implemented with respect to any other method or composition described herein.

The use of the word "a" or "an" when used in conjunction with the term "comprising" in the claims and/or the specification may mean "one," but it is also consistent with the meaning of "one or more," "at least one," and "one or more than one."

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 1A—Reduction of BubR1 and Mad2 levels after transfection with small interfering RNA (siRNA). MCF-7 cells were transfected with siRNA/Mad2 or siRNA/BubR1, resulting in a final concentration of 200 nM for the siRNAs. At the indicated times after transfection, cells were harvested and subjected to protein immunoblot analysis with each antibody and α-tubulin antibody to control for gel loading. FIG. 1B—Cell cycle distribution of cells with suppression of Mad2, BubR1, or both, as measured by DNA content by fluorescence-activated cell sorting as described in herein. MCF-7 cells were transfected and harvested 72 hr after transfection. Numbers indicate percentages of cells in each phase. FIG. 1C—Mitotic indices of each cell after treatment with paclitaxel. Twenty-four hr after transfection, cells were treated with paclitaxel (100 nM) and harvested at the indicated times. FIG. 1D—Cyclin-dependent kinase-1 (Cdk1) activity after treatment with paclitaxel in each cell. Twenty-four hr after transfection, cells were treated with paclitaxel (100 nM) and harvested at the indicated times. Activity of Cdk1 in the lysates was determined as described in Experimental procedures.

FIG. 2A—MCF-7 cells transfected with siRNA/Mad2, BubR1, or both were examined using MTT assay to determine the effects of paclitaxel on cell growth. Twelve hr after transfection, the cells were detached by trypsinization. Twelve hr after seeding, cells were treated with paclitaxel at various concentrations. Bars, standard deviations. FIG. 2B—MCF-7 cells transfected with siRNA/Mad2, BubR1, or both were examined for cell death induced by paclitaxel. Twenty-four hr after transfection, cells were treated with paclitaxel (100 nM) for 48 hr. Cell viability was assessed using trypan blue exclusion assay. Bars, standard deviations.

FIG. 3A—Exogenous Mad2 expression in MCF-7, MCF-10A, T47D, and Ovca432 cells by infection with Ad-EGFP/Mad2. Twenty-four hr after infection at multiplicity of infection values of 25 and 50, 20 μg of each lysate sample was applied and subjected to protein immunoblot analysis with anti-Mad2 antibody. FIG. 3B—Cell cycle distribution of cells with overexpression of Mad2 as measured by DNA content by fluorescence-activated cell sorting. MCF-7, T47D, and Ovca432 cells were harvested 48 hr after infection and subsequently stained with propidium iodide to detect DNA content. Numbers show the percentages of cells in each phase. FIG. 3C—Top: Schedule for combined small interfering RNA (siRNA)/Mad2 transfection and adenovirus infection. Twenty-four hr after transfection of siRNA/Mad2, adenoviral vectors (multiplicity of infection of 50) were delivered over a 24-hr period, and cells were exposed to paclitaxel (100 nM). Bottom: Expression of Mad2 in Mad2-suppressed MCF-7 cells infected with Ad-EGFP/Mad2 or Ad-EGFP/Luc. Cells were harvested at 0, 24, and 48 hr after paclitaxel treatment and subjected to protein immunoblot analysis with each antibodies and α-tubulin antibody to control for gel loading. FIG. 3D—Cyclin-dependent kinase-1 (Cdk1) activity after treatment with paclitaxel in Mad2-suppressed MCF-7 cells infected with Ad-EGFP/Mad2 or Ad-EGFP/Luc. Twenty-four hr after infection with either Ad-EGFP/Mad2 or Ad-EGFP/Luc at a multiplicity of infection of 50, cells were treated with paclitaxel (100 nM) and harvested at the indicated times. Cdk1 activity in the lysate was determined as described herein. FIG. 3E—Paclitaxel-induced cell death in Mad2-suppressed MCF-7 cells infected with Ad-EGFP/Mad2 or Ad-EGFP/Luc. Twenty-four hr after infection, cells were harvested. Forty-eight hr after treatment with paclitaxel, cell viability was assessed using trypan blue exclusion assay. Bars, standard deviations. FIG. 3F—Cyclin-dependent kinase-1 (Cdk1) activity after treatment with paclitaxel in infected T47D and Ovca432 cells. Twenty-four hr after infection with either Ad-EGFP/Mad2 or Ad-EGFP/Luc at a multiplicity of infection of 50, cells were treated with paclitaxel (100 nM) and harvested at the indicated times. Cdk1 activity in the lysate was determined as described herein. FIG. 3G—Paclitaxel-induced cell death in T47D and Ovca432 cells infected with Ad-EGFP/Mad2 or Ad-EGFP/Luc. Cells were harvested 24 hr after infection. Forty-eight hr after treatment with paclitaxel, cell viability was assessed using trypan blue exclusion assay. Bars, standard deviations.

FIG. 4A—Top: Schedule for combined small interfering RNA (siRNA)/BubR1 transfection and adenovirus infection. Twenty-four hr after transfection of siRNA/BubR1, adenoviral vectors (multiplicity of infection of 50) were delivered over a 24-hr period, and cells were exposed to paclitaxel (100 nM). Bottom: Expression of Mad2 and BubR1 in BubR1-suppressed MCF-7 cells infected with Ad-EGFP/Mad2 or Ad-EGFP/Luc. Cells were harvested at the indicated times after paclitaxel treatment and subjected to protein immunoblot analysis with each antibody and α-tubulin antibody to control for gel loading. FIG. 4B—Cdk1 activity after treatment with paclitaxel in BubR1-suppressed MCF-7 cells infected with Ad-EGFP/Mad2 or Ad-EGFP/Luc. Cells were harvested at the indicated times after paclitaxel treatment. Activity of Cdk1 in the lysate was determined as described herein. FIG. 4C—Paclitaxel-induced cell death in BubR1-suppressed MCF-7 cells infected with Ad-EGFP/Mad2 or Ad-EGFP/Luc. Cells were harvested 48 hr after treatment with paclitaxel. Cell viability was assessed by trypan blue exclusion. Bars, standard deviations. FIG. 4D—Cyclin-dependent kinase-1 (Cdk1) activity after treatment of paclitaxel in infected MCF-7 and MCF-10A cells. Twenty-four hr after infection with Ad-EGFP/Mad2 or Ad-EGFP/Luc at a multiplicity of infection of 50, cells were treated with paclitaxel (100 nM) and harvested at the indicated times. Cdk1 activity in the lysate was determined as described herein. FIG. 4E—Paclitaxel-induced cell death in MCF-7 and MCF-10A cells infected with Ad-EGFP/Mad2 or Ad-EGFP/Luc. Cells were harvested 24 hr after infection. Forty-eight hr after treatment with paclitaxel, cell viability was assessed using trypan blue exclusion assay. Bars, standard deviations.

As shown in FIG. 3, susceptible tumor showed a dramatic decrease in tumor volume from 460 mm$^3$ to 120 mm$^3$. By contrast, the volume of resistant tumor remained at 350 mm$^3$ until Day 43.

DESCRIPTION OF PREFERRED EMBODIMENTS

I. The Present Invention

Figure 1A:
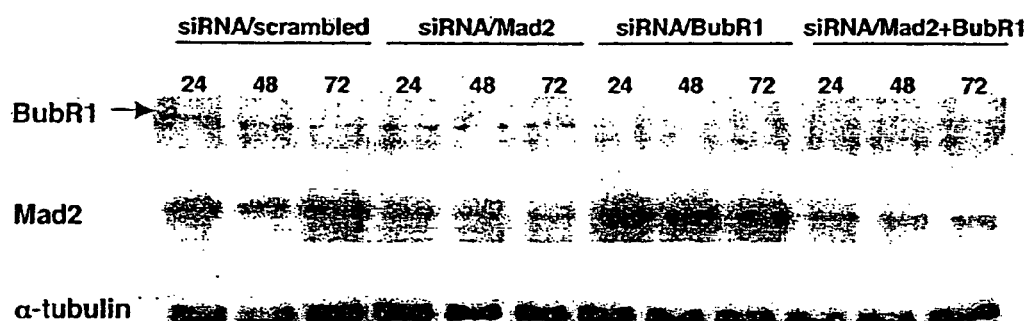
FIGS. 1A-1D. Loss of spindle assembly checkpoint in cells with suppression of Mad2, BubR1, or both.

The invention provides a method for determining taxane chemosensitivity of cancer cells and tissues. The present invention determines that molecules in the spindle assembly checkpoint are required for taxane sensitivity thus, molecules involved in this checkpoint such as, Cdk1 or other molecular markers, are determined to be useful in predicting taxane sensitivity. The present invention therefore provides a method of determining or assessing taxane chemosensitivity by cell-cycle profiling of cancer cells and tissues. Cell cycle profiling was performed by measuring several cell-cycle molecules (also referred herein as parameters) such as CDK1, CDK2, CDK4, and CDK6 for kinase activity measurement; and CDK1, CDK2, CDK4, CDK6, Cyclin B1, Cyclin D1, Cyclin E, p21/Waf1, p27/Kip1, p16, p53 and MAD2 for protein expression measurement. Because the parameters of the cell cycle profiling system involve M-phase regulatory machinery, including MAD2 expression and CDK1 activity, the system is an effective predictor of taxane sensitivity.

II. Taxanes

Taxanes and related active ingredients are produced by plants of the Taxus species and are constituents of different parts of such plants. Taxanes, such as TAXOL® (paclitaxel), are cyclotoxic diterpenes obtained from the yew tree. Taxanes are known in the art to inhibit cell replication on a molecular basis, in that they inhibit growing cells in the G2/M phase of the cell cycle. Thus, taxanes have an anti-tumor effect and are used increasingly for the treatment of a series of carcinomas (ovarian, breast, bronchial and lung carcinomas).

A. Paclitaxel TAXOL®

Paclitaxel, also known as TAXOL® is a diterpene alkaloid thus it possesses a taxane skeleton in its structure. Paclitaxel is extracted from the bark of the Pacific yew (*Taxus brevifolia*) as a natural compound having anti-cancer activity (Fuchs and Johnson, 1978). Paclitaxel works against cancer by interfering with mitosis. Paclitaxel is a taxoid drug, widely used as an effective treatment of primary and metastatic cancers.

Paclitaxel (TAXOL®) is widely used in the treatment of breast, ovarian, and other solid tumors. Randomized clinical trials have shown a survival advantage among patients with primary breast cancer who received paclitaxel in addition to anthracycline-containing adjuvant chemotherapy (Eifel et al., 2001). Furthermore, paclitaxel is effective for both metastatic breast cancer (Holmes et al., 1991; Nabholtz et al., 1996; Bishop et al., 1999) and advanced ovarian cancer (McGuire et al., 1996; Piccart et al., 2000). The antitumor activity of paclitaxel is unique because it promotes microtubule assembly and stabilizes the microtubules, thus preventing mitosis (Huizing et al., 1995). Paclitaxel does this by reversibly and specifically binding to the B subunit of tubulin, forming microtubule polymers thereby stabilizing them against depolymerization and thus leading to growth arrest in the G2/M phase of the cell cycle (Gotaskie and Andreassi, 1994). This makes TAXOL® (paclitaxel) unique in comparison to vincristine and vinblastine which cause microtubule disassembly (Gatzemeier et al., 1995). Additionally, recent evidence indicates that the microtubule system is essential to the release of various cytokines and modulation of cytokine release may play a major role in the drug's antitumor activity (Smith et al., 1995).

However, some patients are resistant to paclitaxel therapy, and the characteristics of patients who will benefit from the drug have not been well defined. Identification of molecular characteristics predictive of paclitaxel sensitivity or resistance could aid in selecting patients to receive this therapy. Thus, in particular embodiments, the present invention relates to paclitaxel sensitivity in a patient having cancer.

Previous reports have demonstrated that paclitaxel resistance is due to a variety of mechanisms such as up-regulation of anti-apoptotic Bcl-2 family members, such as Bcl-2 and Bcl-$X_L$ (Tang et al., 1994); up-regulation of membrane transporters (e.g., mdr-1), resulting in an increased drug efflux (Huang et al., 1997); mutations in beta-tubulin resulting in abolishment of paclitaxel binding (Giannakakou et al., 1997); and up-regulation of ErbB2 (HER2) through inhibition of cyclin-dependent kinase-1 (Cdk1), resulting in delayed mitosis (Yu et al., 1998).

Due to the antimitotic activity of paclitaxel it is a useful cytotoxic drug in treating several classic refractory tumors. Paclitaxel has primarily been use to treat breast cancer and ovarian cancer. It may also be used in treating head and neck cancer, Kaposi's sarcoma and lung cancer, small cell and non-small cell lung cancer. It may also slow the course of melanoma. Response rates to TAXOL® (paclitaxel) treatment varies among cancers. Advanced drug refractory ovarian cancer responds at a 19-36% rate, previously treated metastatic breast cancer at 27-62%, and various lung cancers at 21-37%. TAXOL® (paclitaxel) has also been shown to produce complete tumor remission in some cases (Guchelaar et al., 1994).

Paclitaxel is given intravenously since it irritates skin and mucous membranes on contact. It is typically administered intravenously by a 3 to 24 hour infusion three times per week (Guchelaar et al., 1994).

Paclitaxel (which may include formulations, prodrugs, analogues and derivatives such as, for example, TAXOL™, TAXOTERE™, docetaxel, 10-desacetyl analogues of paclitaxel and 3'N-desbenzoyl-3'N-t-butoxy carbonyl analogues of paclitaxel) may be readily prepared utilizing techniques known to those skilled in the art (see, e.g., Schiff et al., 1979; Long and Fairchild, 1994; Ringel and Horwitz, 1991; Pazdur et al., 1993; PCT Applications. WO 94/07882; WO 94/07881;

WO 94/07880; WO 94/07876; WO 93/23555; WO 93/10076; WO94/00156; WO 93/24476; EP 590267; WO 94/20089; U.S. Pat. Nos. 5,294,637; 5,283,253; 5,279,949; 5,274,137; 5,202,448; 5,200,534; 5,229,529; 5,254,580; 5,412,092; 5,395,850; 5,380,751; 5,350,866; 4,857,653; 5,272,171; 5,411,984; 5,248,796; 5,422,364; 5,300,638; 5,362,831; 5,440,056; 4,814,470; 5,278,324; 5,352,805; 5,059,699; 4,942,184; or obtained from a variety of commercial sources, including for example, Sigma, St. Louis, Mo. (T7402—from *Taxus brevifolia*).

B. Docetaxel/Taxotere

Docetaxel is an antineoplastic agent belonging to the taxoid family. Docetaxel has primarily been use to treat breast cancer, lung cancer, non-small cell lung cancer. In addition, it may be used to treat head and neck cancer, small cell lung cancer, mesothelioma, ovarian cancer, prostate cancer, and urothelial transitional cell cancer. Docetaxel interferes with the growth of cancer cells, which are eventually destroyed. However, as discussed above in regards to paclitaxel therapy, some patients are resistant to docetaxel therapy. Therefore, by assessing or determining the chemosensitivity of this taxane in a cancer patient, this agent can be used more effectively to treat cancer.

Docetaxel is a semi-synthetic drug derived from precursor extracted from the needles of the European yew tree, *Taxus baccata*. The chemical name for docetaxel is (2R,3S)-N-carboxy-3-phenylisoserine, N-tert-butyl ester, 13-ester with 5b-20-epoxy-12a,4,7b,10b,13a-hexahydroxytax-11-en-9-one 4-acetate 2-benzoate, trihydrate. It acts by disrupting the microtubular network that is essential for mitotic and interphase cellular functions. It promotes the assembly of tubulin into stable microtubules and inhibits their disassembly, causing inhibition of cell division and eventual cell death. Both docetaxel and paclitaxel bind to the same microtubule site, although the affinity of docetaxel is 1.9-fold higher. Cross-resistance between docetaxel and paclitaxel does not occur consistently. Docetaxel is a radiation-sensitizing agent. It is cell cycle phase-specific ($G_2$/M phase).

C. Other Taxanes

The present invention also contemplates testing the chemosensitivity of any taxane or compound having a taxane skeleton as is known to one of ordinary skill in the art, including taxane analogues or derivates having anticancer activity. A "taxane compound" may include TAXOL® (paclitaxel), compounds which are structurally similar to TAXOL® (paclitaxel) and/or analogs of TAXOL® (paclitaxel). A "taxane compound" may also include "mimics". "mimics" is intended to include compounds which may not be structurally similar to TAXOL® (paclitaxel) but mimic the therapeutic activity of TAXOL® (paclitaxel) or structurally similar taxane compounds in vivo. The taxane compounds of the present invention are those compounds which are useful for inhibiting tumor growth in subjects (patients) having cancer. The term taxane compound also is intended to include pharmaceutically acceptable salts of the compounds. Taxane compounds have previously been described in U.S. Pat. Nos. 5,641,803, 5,665,671, 5,380,751, 5,728,687, 5,415,869, 5,407,683, 5,399,363, 5,424,073, 5,157,049, 5,773,464, 5,821,263, 5,840,929, 4,814,470, 5,438,072, 5,403,858, 4,960,790, 5,433,364, 4,942,184, 5,362,831, 5,705,503, 5,278,324, 5,840,929, 5,773,464, 5,248,796, 5,821,263, 4,814,470, 5,438,072, 4,942,184, 5,433,364, 5,278,324, 6,362,217, 6,017,935, 5,977,376, 5,912,264, 5,773,464, 5,739,539, 5,698,712, 6,284,746; U.S. Pat. appln. Ser. Nos. 20030144344, 20030130341, 20030134793, 20030130170, 20030130178, 20030124055, and 20020016356; and PCT Appins. WO 95/33740, 96/03394, 95/33736, 93/02067, 94/15929 and 94/15599; all of which are incorporated herein by reference.

Other taxanes may include water soluble compositions of paclitaxel and docetaxel formed by conjugating the paclitaxel or docetaxel to a water soluble polymer such as poly-glutamic acid, poly-aspartic acid or poly-lysine (U.S. Patent Application 20030147807). Derivatives of paclitaxel possess varying degrees of pharmacological activity. Investigations into the synthesis and evaluation of such paclitaxel derivative compounds have been made in an effort to develop safe, convenient, and efficacious drug formulations useful for the treatment of cancer in warm-blooded animals including humans. Since the discovery of paclitaxel, over one hundred compounds having a related structure have been isolated from various species of *Taxus* and/or made synthetically.

One exemplary paclitaxel derivative having desirable antitumor properties, is the compound, 7-O-methylthiomethyl paclitaxel (herein referred to as "7-O-MTM paclitaxel") which differs structurally from paclitaxel at the C-7 position on the taxane ring. 7-O-MTM paclitaxel is a known antitumor agent currently under study in clinical trials. Studies involving 7-O-MTM paclitaxel have shown promising results in the treatment of gastrointestinal and colorectal cancers where paclitaxel has been found to be less effective. It is known that 7-O-MTM paclitaxel may be produced by synthetic processes (U.S. Pat. No. 5,646,176, and WO 96/00724; content of which are each incorporated herein by reference).

Representative examples of paclitaxel derivatives or analogues contemplated in the present invention may include, but are not limited to, 7-deoxy-docetaxol, 7,8-cyclopropataxanes, N-substituted 2-azetidones, 6,7-epoxy paclitaxels, 6,7-modified paclitaxels, 10-desacetoxytaxol, 10-deacetyltaxol (from 10-deacetylbaccatin III), phosphonooxy and carbonate derivatives of TAXOL® (paclitaxel), TAXOL® (paclitaxel) 2',7-di(sodium 1,2-benzenedicarboxylate, 10-desacetoxy-11,12-dihydrotaxol-10,12(18)-diene derivatives, 10-desacetoxytaxol, Protaxol (2'- and/or 7-O-ester derivatives), (2'- and/or 7-O-carbonate derivatives), asymmetric synthesis of TAXOL® (paclitaxel) side chain, fluoro taxols, 9-deoxotaxane, (13-acetyl-9-deoxobaccatine III, 9-deoxotaxol, 7-deoxy-9-deoxotaxol, 10-desacetoxy-7-deoxy-9-deoxotaxol; derivatives containing hydrogen or acetyl group and a hydroxy and tert-butoxycarbonylamino, sulfonated 2'-acryloyltaxol and sulfonated 2'-O-acyl acid TAXOL® (paclitaxel) derivatives, succinyltaxol, 2'-γ-aminobutyryltaxol formate, 2'-acetyl TAXOL® (paclitaxel), 7-acetyl TAXOL® (paclitaxel), 7-glycine carbamate TAXOL® (paclitaxel), 2'-OH-7-PEG(5000) carbamate TAXOL® (paclitaxel), 2'-benzoyl and 2',7-dibenzoyl TAXOL® (paclitaxel) derivatives; other prodrugs (2'-acetyltaxol; 2',7-diacetyltaxol; 2' succinyltaxol; 2'-(beta-alanyl)-taxol); 2' gamma-aminobutyryltaxol formate; ethylene glycol derivatives of 2'-succinyltaxol; 2'-glutaryltaxol; 2'-(N,N-dimethylglycyl) TAXOL® (paclitaxel); 2'-(2-(N,N-dimethylamino)propionyl)taxol; 2' orthocarboxybenzoyl TAXOL® (paclitaxel); 2' aliphatic carboxylic acid derivatives of TAXOL® (paclitaxel); prodrugs {2'(N,N-diethylaminopropionyl)taxol, 2'(N,N-dimethylglycyl)taxol, 7-(N,N-dimethylglycyl)taxol, 2',7-di-(N,N-dimethylglycyl)taxol, 7-(N,N-diethylaminopropionyl)taxol, 2',7-di(N,N-diethylaminopropionyl)taxol, 2'-(L-glycyl) taxol, 7-(L-glycyl)taxol, 2',7-di(L-glycyl)taxol, 2'-(L-alanyl) taxol, 7-(L-alanyl)taxol, 2',7-di(L-alanyl)taxol, 2'-(L-leucyl) taxol, 7-(L-leucyl)taxol, 2',7-di(L-leucyl)taxol, 2'-(L-isoleucyl)taxol, 7-(L-isoleucyl)taxol, 2',7-di(L-isoleucyl) taxol, 2'-(L-valyl)taxol, 7-(L-valyl)taxol, 2',7-di(L-valyl) taxol, 2'-(L-phenylalanyl)taxol, 7-(L-phenylalanyl)taxol, 2',7-di(L-phenylalanyl)taxol, 2'-(L-prolyl)taxol, 7-(L-prolyl) taxol, 2',7-di(L-prolyl)taxol, 2'-(L-lysyl)taxol, 7-(L-lysyl) taxol, 2',7-di(L-lysyl)taxol, 2'-(L-glutamyl)taxol, 7-(L-glutamyl)taxol, 2',7-di(L-glutamyl)taxol, 2'-(L-arginyl) taxol, 7-(L-arginyl)taxol, 2',7-di(L-arginyl)taxol); TAXOL® (paclitaxel) analogs with modified phenylisoserine side chains, taxotere, (N-debenzoyl-N-tert-(butoxycaronyl)-10-deacetyltaxol, and taxanes (e.g., baccatin III, cephalomannine, 10-deacetylbaccatin III, brevifoliol, yunantaxusin and taxusin); and other taxane analogues and derivatives, including 14-beta-hydroxy-10 deacetybaccatin III, debenzoyl-2-acyl paclitaxel derivatives, benzoate paclitaxel derivatives, phosphonooxy and carbonate paclitaxel derivatives, sulfonated 2'-acryloyltaxol; sulfonated 2'-O-acyl acid paclitaxel derivatives, 18-site-substituted paclitaxel derivatives, chlorinated paclitaxel analogues, C4 methoxy ether paclitaxel derivatives, sulfenamide taxane derivatives, brominated paclitaxel analogues, Girard taxane derivatives, nitrophenyl paclitaxel, 10-deacetylated substituted paclitaxel derivatives, 14-beta-hydroxy-10 deacetylbaccatin III taxane derivatives, C7 taxane derivatives, C10 taxane derivatives, 2-debenzoyl-2-acyl taxane derivatives, 2-debenzoyl and -2-acyl paclitaxel derivatives, taxane and baccatin III analogs bearing new C2 and C4 functional groups, n-acyl paclitaxel analogues, 10-deacetylbaccatin III and 7-protected-10-deacetylbaccatin III derivatives from 10-deacetyl TAXOL® (paclitaxel) A, 10-deacetyl TAXOL® (paclitaxel) 1 B, and 10-deacetyl TAXOL® (paclitaxel), benzoate derivatives of TAXOL® (paclitaxel), 2-aroyl-4-acyl paclitaxel analogues, orthro-ester paclitaxel analogues, 2-aroyl-4-acyl paclitaxel analogues and 1-deoxy paclitaxel and 1-deoxy paclitaxel analogues.

III. Obtaining Samples for Cell Cycle Profiling

The present invention contemplates obtaining a sample such as a cell, tissue or organ sample. A sample of the present invention may be obtained from a patient by several means. For example, a cell, organ or tissue sample of the invention may be obtained by a biopsy. A biopsy is the removal of a sample from the body. Biospies that may be employed in the present invention include punch biopsy or needle biospy, but are not limited to such. A sample containing a cell cycle molecule may be obtained by any method as is know in the art. A blood or serum sample may be collected using venipuncture. Using this method, blood is drawn directly from a blood vessel in the arm of an individual through a needle placed in a single vein. The blood may then be collected in a glass or plastic tube.

A. Punch Biopsy and Cone Biopsy The present invention contemplates the use of punch or cone biopsy to obtain a sample such as a cancer sample. Punch biopsy is typically used to obtain samples of skin rashes, moles, small tissue samples from the cervix and other small masses. After a local anesthetic is injected, a biopsy punch, (3 mm to 4 mm or 0.15 inch in diameter), is used to cut out a cylindrical piece of skin. The opening is typically closed with a suture and heals with minimal scarring.

Cone Biopsy on the other hand, is used to obtain a piece of tissue which is cylindrical or cone shaped. The advantage of cone biopsy is that it provides a large sample of tissue for analysis.

B. Needle Biopsy

1. Core Needle Biopsy

Core needle biopsy (or core biopsy) is performed by inserting a small hollow needle through the skin and into the organ. The needle is then advanced within the cell layers to remove a sample or core. The needle may be designed with a cutting tip to help remove the sample of tissue. Core biopsy is often performed with the use of spring loaded gun to help remove the tissue sample.

Core biopsy is typically performed under image guidance such as CT imaging, ultrasound or mammography. The needle is either placed by hand or with the assistance of a sampling device. Multiple insertions are often made to obtain sufficient tissue, and multiple samples are taken. As tissue samples are taken, a click may be heard from the sampling instrument.

Core biopsy is sometimes suction assisted with a vacuum device (vacuum assisted biopsy). This method enables the removal of multiple samples with only one needle insertion. Unlike core biopsy, the vacuum assisted biopsy probe is inserted just once into the tissue through a tiny skin nick. Multiple samples are then taken using a rotation of the sampling needle aperture (opening) and with the assistance of suction. Thus, core needle biospy or vacuum assisted needle biopsy may be employed in the present invention to obtain a tissue sample.

2. Aspiration/Fine Needle Aspiration (FNA) Biopsy

Aspiration biopsy, also referred to as Fine Needle Aspiration (FNA), is performed with a fine needle attached to a syringe. Aspiration biopsy or FNA may be employed in the present invention to obtain a cancer sample. FNA biopsy is a percutaneous (through the skin) biopsy. FNA biopsy is typically accomplished with a fine gauge needle (22 gauge or 25 gauge). The area is first cleansed and then usually numbed with a local anesthetic. The needle is placed into the region of organ or tissue of interest. Once the needle is placed a vacuum is created with the syringe and multiple in and out needle motions are performed. The cells to be sampled are sucked into the syringe through the fine needle. Three or four samples are usually made.

Organs that are not easily reached such as the pancreas, lung, and liver are good candidates for FNA. FNA procedures are typically done using ultrasound or computed tomography (CT) imaging.

C. Endoscopic Biopsy

Endoscopic biopsy is a very common type of biopsy that may be employed in the present invention to obtain a cancer sample. Endoscopic biopsy is done through an endoscope (a fiber optic cable for viewing inside the body) which is inserted into the body along with sampling instruments. The endoscope allows for direct visualization of an area on the lining of the organ of interest; and collection or pinching off of tiny bits of tissue with forceps attached to a long cable that runs inside the endoscope of the sample. Endoscopic biopsy may be performed on the gastrointestinal tract (alimentary tract endoscopy), urinary bladder (cystoscopy), abdominal cavity (laparoscopy), joint cavity (arthroscopy), mid-portion of the chest (mediastinoscopy), or trachea and bronchial system (laryngoscopy and bronchoscopy), either through a natural body orifice or a small surgical incision.

D. Surface Biopsy

Surface biopsy may be employed in the present invention to obtain a cancer sample. This technique involves sampling or scraping of the surface of a tissue or organ to remove cells. Surface biopsy is often performed to remove a small piece of skin.

IV. Cell-Cycle Molecules (Parameters)

In assessing or determining taxane chemosensitivity, the present invention assesses or determines the expression level and activity of cell-cycle molecules or factors in cancer cells of a patient.

There mainly exist two groups of cell cycle regulatory factors in cells. One is a group of kinases which are positive regulatory factors and are referred to as cyclin-dependent kinases (CDKs), and the other is a group of CDK inhibitors (CDKIs), which are negative regulatory factors. The CDKs exist in cytoplasm as an inactive form. The CDKs are activated, e.g., phosphorylated, and move into nuclei in the cells. In the nuclei, the CDKs bind to cyclin molecules to form complexes with cyclin (referred to as activated CDKs herein) and positively regulate the progress of the cell cycle at various steps of the cell cycle. On the other hand, the CDKIs inactivate the CDKs by binding to the activated CDKs or CDK simple substances, thereby negatively regulating the cell cycle.

The CDK1 kinase, combined with mitotic cyclins, is a universal master kinase required for the regulation of mitosis, where paclitaxel attacks. This kinase becomes activated in the G2 phase of the cell cycle, and promotes breakdown of the nuclear envelope, condensation of the chromatin, and formation of the spindle apparatus in early mitosis. In contrast, to exit metaphase, CDK1 has to be inactivated through the degradation of its assembly partner, cyclin B, by APC-proteasome pathway. CDK1 activity remains high until the mitotic spindle becomes completely attached to the kinetocore.

A. Cyclin Dependent Kinases (CDKs)

Seven types of CDKs are known, i.e., CDK1, CDK2, CDK3, CDK4, CDK5, CDK6 and CDK7 to which different cyclins are bound. More particularly, CDK1 binds to cyclin A or B, CDK2 binds to cyclin A or E, and CDK4 and CDK6 bind to cyclin D1, D2 or D3, to be activated. The activated CDKs control specific phases of the cell cycle. Thus, the cell cycle is controlled and the cell proliferation is regulated by activation of different types of CDKs. The activated CDKs phosphorylates serine residue and threonine residue in a protein as a substrate. In an in vitro reaction system, the activated CDK1 and CDK2 react well on histone H1 as a substrate and the activated CDK 4 and CDK6 react well on Rb (retinoblastoma protein) as a substrate. In an in vivo cell cycle regulation, it is considered that the activated CDKs require Rb as a physiologic substrate, but it is not known what other proteins act as substrates.

As described above, the CDKs and cyclins regulate the cell cycle in close association with each other. The multiplication of cyclin D1 gene is observed in a great number of cases of esophageal cancer, while over expression of cyclin D1 gene is observed in a great number of cases of stomach cancer and colon cancer. On the other hand, the multiplication of cyclin E gene is observed in stomach cancer and colon cancer but is not observed in esophageal cancer. Excessive expression of cyclin E in stomach and large bowel takes place with great frequency in cases of adenoma and adenocarcinoma and shows a significant correlation with malignancy such as invasion, progress of stages, metastasis and the like. The expression and kinase activity of CDK1 are remarkably accelerated in most cases of stomach cancer and colon cancer as compared with normal mucosal tissue. It is known that augmented expression of cyclin genes correlates with the progress and malignancy of various cancers (see Wataru et al., 2000).

Therefore, it is expected that assessing, determining or measuring the expression level or activity of the individual species of CDKs will provide cell cycle profiling of cancer cells in a patient to a taxane, thereby predicting or diagnosing a cancer. In other words, generally at the R point, the expression of CDK2 decreases and the cell cycle arrest and the division of cells is controlled. However, if the expression of CDK2 increases at the R point, it means that the cell cycle fails to stop, i.e., it means a state of a disease such as cancer.

Usually, the activity of the CDKs is determined using radioisotopes. More particularly, in the presence of a CDK which is extracted from a cell lysate by an immunoprecipitation method using an anti-CDK antibody and whose activity is unknown $^{32}$P-labelled adenosine 5'-O-(3-triphosphate) (ATP) is reacted with serine residue or threonine residue in a substrate to introduce monophosphate group derived from the $^{32}$P-labelled ATP. The amount of $^{32}$P taken by the substrate is detected by autoradiography or by a scintillation counter. Thereby the amount of the phosphorylated substrate is measured and the activity of the CDK is calculated from the amount of the phosphorylated substrate.

B. CDK Inhibitors (CDKIs)

$p16^{INK4}$ belongs to a newly described class of CDK-inhibitory proteins that also includes $p16^{B}$, p19, $p21^{WAF1}$, and $p27^{KIP1}$. The $p16^{INK4}$ gene maps to 9p21, a chromosome region frequently deleted in many tumor types. Homozygous deletions and mutations of the $p16^{INK4}$ gene are frequent in human tumor cell lines. This suggested that the $p16^{INK4}$ gene is a tumor suppressor gene. This interpretation has been challenged, however, by the observation that the frequency of the $p16^{INK4}$ gene alterations is much lower in primary uncultured tumors than in cultured cell lines (Caldas et al., 1994; Cheng et al., 1994; Hussussian et al., 1994; Kamb et al., 1994a; Kamb et al., 1994b; Mori et al., 1994; Okamoto et al., 1994; Nobori et al., 1995; Orlow et al., 1994; Arap et al., 1995). Restoration of wild-type $p16^{INK4}$ function by transfection with a plasmid expression vector reduced colony formation by some human cancer cell lines (Okamoto, 1994; Arap, 1995).

Another inhibitor of cellular proliferation is p16. The major transitions of the eukaryotic cell cycle are triggered by cyclin-dependent kinases, or CDK's. One CDK, cyclin-dependent kinase 4 (CDK4), regulates progression through the $G_1$. The activity of this enzyme may be to phosphorylate Rb at late $G_1$. The activity of CDK4 is controlled by an activating subunit, D-type cyclin, and by an inhibitory subunit, the $p16^{INK4}$ has been biochemically characterized as a protein that specifically binds to and inhibits CDK4, and thus may regulate Rb phosphorylation (Serrano et al., 1993; Serrano et al., 1995). Since the $p16^{INK4}$ protein is a CDK4 inhibitor (Serrano, 1993), deletion of this gene may increase the activity of CDK4, resulting in hyperphosphorylation of the Rb protein. p16 also is known to regulate the function of CDK6.

$p21^{WAF1/CIP1}$ was initially identified as a p53-inducible protein. Loss of p53 is a common phenomenon in tumor cells, resulting in changes in the cellular response to radiation or chemotherapy. Cells that lack p53-mediated cell cycle checkpoints become increasingly genetic unstable and less prone to apoptosis. In response to DNA damage, it has been demonstrated that p21 binds to various cyclin/CDK complexes and inhibits the activity of these complexes, resulting in suppression of cell cycle progression, in a p53-dependent manner. Recently, it has also been shown that upregulation of $p21^{WAF1/CIP1}$ can be accomplished by other cis or trans elements besides p53.

C. Mitotic Spindle Assembly Checkpoint Molecules

The mitotic spindle assembly checkpoint monitors both the attachment of chromosomes to the mitotic spindle and the tension across the sister chromatid generated by microtubules to prevent premature chromosomal segregation. When a drug, such as paclitaxel, stabilizes microtubules and interferes with the dynamic changes that occur during formation of the mitotic spindle, the spindle assembly checkpoint is activated to make cells arrest at mitosis.

The molecular components of the mitotic spindle assembly checkpoint were initially identified in *Saccharomyces cerevi-*

*siae.* Mammalian homologues of the checkpoint proteins include Mad1, Mad2, BubR1, Bub3, and Mps1 (Li and Benezra, 1996; Jin et al., 1998; Taylor et al., 1998; Chan et al., 1999). The checkpoint machinery is a protein complex composed of Mad1, Mad2, BubR1, Bub3 and cdc20, located at the kinetocore of the chromosome. The target of this checkpoint is the anaphase-promoting complex (APC) and its co-activator Cdc20. Mad2 and BubR1 are located downstream and appear to be the major proteins of this machinery, interacting with Cdc20 directly and inhibiting APC activity cooperatively (Fang et al., 1998; Sudakin et al., 2001; Tang et al., 2001; Fang, 2002). In tumor cells, defects in the checkpoint are often observed, and these are believed to induce genome instability.

V. Methods of Determining Expression or Activity of Cell Cycle Parameters

A. Cell Cycle Profiling System

In order to identify a cell cycle molecule(s) involved in taxane chemosensitivity, the present invention employs a multi-parameter analysis for cell-cycle profilfing. This system may employ an apparatus, as described in JP Patent Application 200348653, and incorporated herein in its entirety, based on dot-blot technology, with which to rapidly, quantitatively and automatically assay for protein expression and activity in small clinical samples of normal and carcinoma tissues without the use of isotopes. Tissue samples of only 2 mm$^3$ are sufficient to measure the activities of CDKs, and the expression of other kinds of proteins. This cell cycle profiling system/device has a variety of possible applications such as, measurement of the activities of other kinases or proteins in the diagnosis of many diseases, or in assessing prognoses or a patient's sensitivity to various therapies, including molecular-targeting therapies. This device/system may also be used for the diagnosis of risk factors for diseases in individuals.

1. Methods of Measuring Protein Expression

The principles of the assay protocols used in this invention are briefly described below. Protein expression of cell cycle molecules (parameters) may be measured by a new technology named CPDIB (crude protein direct blotting, U.S. Ser. No. 10/423,892; incorporated herein by reference in its entirety) and is based on dot-blot technology. The analysis comprises only three steps: direct immobilization of crude cell lysate on a hydrophobic membrane, reaction of the primary antibody, and detection of the bound primary antibody; e.g. by sequential reaction of biotinylated secondary antibody and fluorescein-labeled streptavidin. The total assay time is within three hours. Relative fluorescence units and amounts of standard recombinant proteins are verified to be linearly related. The assay conditions for MAD2 are now being optimized. The major advantage of the system is that the addition of new parameters for profiling is much easier than developing a new Sandwich ELISA system, as the system only requires one specific polyclonal antibody against one target molecule.

The measurement procedures for both activity and expression were developed for automated analysis. Lysates of pieces (2 mm$^3$) of surgically dissected tissues may be prepared using a newly developed tissue-homogenizer (Sysmex, Kobe, Japan) with lysis buffer (0.1% NP-40, 20 mM Tris-HCl [pH 7.4], 150 mM NaCl, 2% Proteinase Inhibitor Cocktail (Sigma, St Louis, Mo.)). The homogenizer removes insoluble materials automatically on a filter disk. Protein concentrations are analyzed (DC Kit, Pierce, Rockford, Ill.), and 2.5 µg of total protein is applied to the 78 µl well (3 mm [w]×5 mm [l]×7 mm [d]) of a newly developed 5×7 cm$^2$ dot-blot device (Sysmex) with a hydrophobic membrane (PVDF with 0.22 µm pores; Millipore, Billerica, Mass.). The target protein in the crude sample bound to the membrane may be quantitatively detected by sequential reactions with anti-CDK antibodies (Santa Cruz Biotechnology, Santa Cruz, Calif.), biotinylated secondary antibody (Santa Cruz Biotechnology), and fluorescein-labeled streptavidin (Vector, Burlingame, Calif.). Between each reaction, the well is automatically washed with TBS solution (25 mM Tris-HCl [pH 7.4], 150 mM NaCl). Fluorescent images of the membranes are analyzed using an image analyzer (Bio-Rad, Hercules, Calif., USA), and the intensity of dots quantified by 'Quantity One' (Bio-Rad). Relative fluorescence units (RFUs) and the amounts of standard recombinant proteins (Santa Cruz Biotechnology) are linearly correlated in the standardized ranges (e.g., CDK1, 2.5-25 ng/dot; CDK2, 1.0-10 ng/dot; CDK4, 1.0-10 ng/dot; CDK6, 2.5-25 ng/dot).

2. Measuring Kinase Activity

For the enzyme assay of CDKs, a non-radioisotopic CDK assay was used (U.S. Patent Application 20020164673). The assay comprises the following steps: precipitation of CDK molecules with the corresponding antibodies (e.g., anti-CDK1, anti-CDK2, anti-CDK4, or anti-CDK6 antibodies) and protein-A beads. Reacting the substrate mixture containing protein substrate and adenosine 5'-O-(3-thiotriphosphate) (ATP-γS) in kinase buffer in order to introduce a monothiophosphate group into a serine or threonine residue of the substrate (Histone H1 may be used as the protein substrate for CDK1 and CDK2, and recombinant RB protein (amino acids 769-921) for CDK4 and CDK6). Labeling the substrate by coupling a labeling fluorophore or a labeling enzyme with a sulfur atom of the introduced monothiophosphate group. Measuring the amount of fluorescence from the labeling fluorophore labeling the substrate, or reacting the labeling enzyme labeling the substrate with a substance which generates an optically detectable product by reaction with the labeling enzyme and optically measuring the amount of the generated product. Calculating the activity of the cyclin-dependent kinase from the measured amount of fluorescence or the measured amount of the generated product with reference to a pre-produced reference curve.

Cell lysates are prepared as described for expression analysis. The CDK molecules are selectively precipitated from 100 µg of lysate total protein with 2 µg of the corresponding antibodies (anti-CDK1, -2, -4, or -6 antibodies; Santa Cruz Biotechnology) and 20 µl of protein A beads (Amersham Pharmacia, Uppsala, Sweden) for 1 h at 4° C. After three washes with washing buffer (0.1% NP-40, 50 mM Tris-Cl [pH 7.4]), 50 µl of the substrate mixture containing 10 µg of protein substrate, 5 mM adenosine 5'-O-(3-thiotriphosphate) (Sigma), 20 mM Tris-Cl (pH 7.4), and 0.1% Triton X-100, is added to the beads and incubated under continuous shaking at 37° C. for 10 min. Histone H1 (Upstate Biotechnology, Lake Placid, N.Y.) may be used as the protein substrate for CDK1 and CDK2, and recombinant RB protein (amino acids 769-921) for CDK4 and CDK6. After the beads are removed, the introduced monothiophosphates in the substrate are further labeled by incubation with 10 mM iodoacetyl-biotin (Pierce) in coupling buffer (100 mM Tris-Cl [pH 8.5], 1 mM EDTA) for 90 min in the dark at room temperature. The reaction is quenched with β-mercaptoethanol, and 0.4 µg of the substrate is applied to the wells of the dot-blot device (Sysmex). The wells are blocked with 4% bovine serum albumin (BSA) for 30 min, then incubated with avidin-FITC (Vector) for 1 h at 37° C. After the membrane is washed, the images are evaluated using an image analyzer (Bio-Rad), and the fluorescence intensity of the dots is quantified using 'Quantity One' (Bio-Rad). The activity is calculated with a standard curve prepared with CDK activities corresponding to 0, 12.5, 25, 50, 100, and 150 µg of protein extracted from a cancer cell line. One unit (U) is equivalent to the kinase activity of 1 µg of total protein from the cells.

VI. Pharmaceutical Compositions, Delivery, and Treatment Regimens

In an embodiment of the present invention, a method of effectively treating and preventing a cancer based on the assessment of taxane chemosensitivity of a patient having the cancer is contemplated. Examples of cancers contemplated for treatment include lung cancer, head and neck cancer, breast cancer, pancreatic cancer, prostate cancer, renal cancer, bone cancer, testicular cancer, cervical cancer, gastrointestinal cancer, lymphomas, pre-neoplastic lesions in the lung, colon cancer, melanoma, bladder cancer and any other neoplastic diseases.

An effective amount of the pharmaceutical taxane composition, generally, is defined as that amount sufficient to detectably and repeatedly ameliorate, reduce, minimize or limit the extent of the disease or condition or symptoms thereof. More rigorous definitions may apply, including elimination, eradication or cure of disease. Preferably, patients will have adequate bone marrow function (defined as a peripheral absolute granulocyte count of >2,000/mm$^3$ and a platelet count of 100,000/mm$^3$), adequate liver function (bilirubin <1.5 mg/dl) and adequate renal function (creatinine <1.5 mg/dl).

A. Taxane Administration

To kill cells, inhibit cell growth, inhibit metastasis, decrease tumor or tissue size and otherwise reverse or reduce the malignant phenotype of tumor cells, using the methods and compositions of the present invention, one would generally contact a cancer cell with the taxane compound. The routes of administration will vary, naturally, with the location and nature of the lesion, and include, e.g., intradermal, transdermal, parenteral, intravenous, intramuscular, intranasal, subcutaneous, percutaneous, intratracheal, intraperitoneal, intratumoral, perfusion, lavage, direct injection, and oral administration and formulation. Any of the formulations and routes of administration discussed with respect to the treatment or diagnosis of cancer may also be employed with respect to neoplastic diseases and conditions.

Intratumoral injection, or injection into the tumor vasculature is specifically contemplated for discrete, solid, accessible tumors. Local, regional or systemic administration also may be appropriate. For tumors of >4 cm, the volume to be administered will be about 4-10 ml (preferably 10 ml), while for tumors of <4 cm, a volume of about 1-3 ml will be used (preferably 3 ml). Multiple injections delivered as single dose comprise about 0.1 to about 0.5 ml volumes. The viral particles may advantageously be contacted by administering multiple injections to the tumor, spaced at approximately 1 cm intervals.

In the case of surgical intervention, the present invention may be used preoperatively, to render an inoperable tumor subject to resection. Alternatively, the present invention may be used at the time of surgery, and/or thereafter, to treat residual or metastatic disease. For example, a resected tumor bed may be injected or perfused with a formulation comprising a taxane compound. The perfusion may be continued post-resection, for example, by leaving a catheter implanted at the site of the surgery. Periodic post-surgical treatment also is envisioned.

Continuous administration also may be applied where appropriate, for example, where a tumor is excised and the tumor bed is treated to eliminate residual, microscopic disease. Delivery via syringe or catherization is preferred. Such continuous perfusion may take place for a period from about 1-2 hr, to about 2-6 hr, to about 6-12 hr, to about 12-24 hr, to about 1-2 days, to about 1-2 wk or longer following the initiation of treatment. Generally, the dose of the taxane composition via continuous perfusion will be equivalent to that given by a single or multiple injections, adjusted over a period of time during which the perfusion occurs. It is further contemplated that limb perfusion may be used to administer taxane compositions of the present invention.

Treatment regimens may vary as well, and often depend on tumor type, tumor location, disease progression, and health and age of the patient. Obviously, certain types of tumor will require more aggressive treatment, while at the same time, certain patients cannot tolerate more taxing protocols. The clinician will be best suited to make such decisions based on the assessment of taxane chemosensitivity by cell cycle profiling and the known efficacy and toxicity (if any) of the taxane formulations.

In certain embodiments, the tumor being treated may not, at least initially, be resectable. Treatments with therapeutic compositions may increase the resectability of the tumor due to shrinkage at the margins or by elimination of certain particularly invasive portions. Following treatments, resection may be possible. Additional treatments subsequent to resection will serve to eliminate microscopic residual disease at the tumor site.

A typical course of treatment, for a primary tumor or a post-excision tumor bed, will involve multiple doses. Typical primary tumor treatment involves a 6 dose application over a two-week period. The two-week regimen may be repeated one, two, three, four, five, six or more times. During a course of treatment, the need to complete the planned dosings may be re-evaluated.

The treatments may include various "unit doses." Unit dose is defined as containing a predetermined-quantity of the taxane composition. The quantity to be administered, and the particular route and formulation, are within the skill of those in the clinical arts. A unit dose need not be administered as a single injection but may comprise continuous infusion over a set period of time.

B. Injectable Compositions and Formulations

The preferred method for the delivery of a taxane composition to cancer cells in the present invention is systemically or via intratumoral injection. However, the pharmaceutical compositions disclosed herein may alternatively be administered parenterally, intravenously, intradermally, intramuscularly, transdermally or even intraperitoneally as described in U.S. Pat. No. 5,543,158; U.S. Pat. No. 5,641,515 and U.S. Pat. No. 5,399,363 (each specifically incorporated herein by reference in its entirety).

Injection of a taxane composition may be delivered by syringe or any other method used for injection of a solution, as long as the compound can pass through the particular gauge of needle required for injection. A novel needleless injection system has been described (U.S. Pat. No. 5,846,233) having a nozzle defining an ampule chamber for holding the solution and an energy device for pushing the solution out of the nozzle to the site of delivery. A syringe system has also been described for use in gene therapy that permits multiple injections of predetermined quantities of a solution precisely at any depth (U.S. Pat. No. 5,846,225).

Solutions of the active compounds as free base or pharmacologically acceptable salts may be prepared in water suitably mixed with a surfactant, such as hydroxypropylcellulose. Dispersions may also be prepared in glycerol, liquid polyethylene glycols, and mixtures thereof and in oils. Under ordinary conditions of storage and use, these preparations contain a preservative to prevent the growth of microorganisms. The pharmaceutical forms suitable for injectable use include sterile aqueous solutions or dispersions and sterile powders for the extemporaneous preparation of sterile injectable solutions or dispersions (U.S. Pat. No. 5,466,468, specifically incorporated herein by reference in its entirety). In all cases the form must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol, and the like), suitable mixtures thereof, and/or vegetable oils. Proper fluidity may be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous, intratumoral and intraperitoneal administration. In this connection, sterile aqueous media that can be employed will be known to those of skill in the art in light of the present disclosure. For example, one dosage may be dissolved in 1 ml of isotonic NaCl solution and either added to 1000 ml of hypodermolysis fluid or injected at the proposed site of infusion, (see for example, "Remington's Pharmaceutical Sciences" 15th Edition, pages 1035-1038 and 1570-1580). Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by FDA Office of Biologics standards.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

The compositions disclosed herein may be formulated in a neutral or salt form. Pharmaceutically-acceptable salts, include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like. Upon formulation, solutions will be administered in a manner compatible with the dosage formulation and in such amount as is therapeutically effective. The formulations are easily administered in a variety of dosage forms such as injectable solutions, drug release capsules and the like.

As used herein, "carrier" includes any and all solvents, dispersion media, vehicles, coatings, diluents, antibacterial and antifungal agents, isotonic and absorption delaying agents, buffers, carrier solutions, suspensions, colloids, and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions.

The phrase "pharmaceutically-acceptable" or "pharmacologically-acceptable" refers to molecular entities and compositions that do not produce an allergic or similar untoward reaction when administered to a human. The preparation of an aqueous composition that contains a protein as an active ingredient is well understood in the art. Typically, such compositions are prepared as injectables, either as liquid solutions or suspensions; solid forms suitable for solution in, or suspension in, liquid prior to injection can also be prepared.

VII. Combination Treatments

The compounds and methods of the present invention may be used in the context of neoplastic diseases/conditions including cancer. Types of cancers may include lung cancer, head and neck cancer, breast cancer, pancreatic cancer, prostate cancer, renal cancer, bone cancer, testicular cancer, cervical cancer, gastrointestinal cancer, lymphomas, pre-neoplastic lesions in the lung, colon cancer, melanoma, bladder cancer and any other neoplastic diseases. In order to increase the effectiveness of a treatment with the taxane compositions of the present invention, such as paclitaxel, docetaxel or analogues thereof, it may be desirable to combine these compositions with other agents effective in the treatment of those diseases and conditions. For example, the treatment of a cancer may be implemented with taxane compounds of the present invention and other anti-cancer therapies, such as anti-cancer agents or surgery.

Various combinations may be employed; for example, the taxane composition is "A" and the anti-cancer therapy is "B":
A/B/A B/A/B B/B/A A/A/B A/B/B B/A/A A/B/B/B B/A/B/B B/B/B/A B/B/A/B A/A/B/B A/B/A/B A/B/B/A B/B/A/A B/A/B/A B/A/A/B A/A/A/B B/A/A/A A/B/A/A A/A/B/A Administration of a therapeutic composition of the present invention to a patient will follow general protocols for the administration of that particular secondary therapy, taking into account the toxicity, if any, of the taxane treatment. It is expected that the treatment cycles would be repeated as necessary. It also is contemplated that various standard therapies, as well as surgical intervention, may be applied in combination with the described cancer cell.

A. Anti-Cancer Therapies

An anti-cancer therapy as contemplated for use with the present invention would be capable of negatively affecting cancer in a subject, for example, by killing cancer cells, inducing apoptosis in cancer cells, reducing the growth rate of cancer cells, reducing the incidence or number of metastases, reducing tumor size, inhibiting tumor growth, reducing the blood supply to a tumor or cancer cells, promoting an immune response against cancer cells or a tumor, preventing or inhibiting the progression of cancer, or increasing the lifespan of a subject with cancer. Anti-cancer therapy include biological agents (biotherapy), chemotherapy agents, and radiotherapy agents. The combination of chemotherapy with biological therapy is known as biochemotherapy.

Thus, the present invention contemplates a taxane composition and an anti-cancer agent provided in a combined amount effective to kill or inhibit proliferation of the cell. This process may involve contacting the cells with the taxane and the agent(s) or factor(s) at the same time. This may be achieved by contacting the cell with a single composition or pharmacological formulation that includes both the taxane and the other agent, or by contacting the cell with two distinct compositions or formulations, at the same time, wherein one composition includes the taxane and the other includes the anticancer agent(s).

1. Chemotherapy

It is also contemplated in the present invention a taxane may be used in combination with chemotherapeutic agents. Such chemotherapeutic agents may include, for example, cisplatin (CDDP), carboplatin, procarbazine, mechlorethamine, cyclophosphamide, camptothecin, ifosfamide, melphalan, chlorambucil, busulfan, nitrosurea, dactinomycin, daunorubicin, doxorubicin, bleomycin, plicomycin, mitomycin, etoposide (VP16), tarnoxifen, raloxifene, estrogen receptor binding agents, TAXOL® (paclitaxel), gemcitabien, navelbine, farnesyl-protein transferase inhibitors, transplatinum, 5-fluorouracil, vincristine, vinblastine and methotrexate, Temazolomide (an aqueous form of DTIC), or any analog or derivative thereof. One example of a chemotherapuetuc agent currently used to treat pancreatic cancer is gemcitaben. Other studies employ high doses of 5-Fluorouracil (5-FU) for treatment of advanced pancreatic cancer.

The taxane may also be used in combination with other chemotherapeutic agents such as protein tyrosine kinase inhibitors. Such inhibitors may suitably include imatinib or imatinib mesylate (STI-571, Gleevec™; Norvartis, OSI-774 (Tarceva™; OSI Pharmaceuticals, Inc.), ZD-1839 (Iressa®); AstraZeneca, Inc.), SU-101 (Sugen, Inc.) and CP-701 (Cephalon, Inc.).

2. Radiotherapy

Another therapy that may be used in the present invention in conjunction with a taxane, in treating a patient having cancer, is radiotherapy. It is contemplated that radiotherapeutic factors that may be employed in the present invention are factors that cause DNA damage and have been used extensively, such as γ-rays, X-rays, and/or the directed delivery of radioisotopes to tumor cells. Other forms of DNA damaging factors are also contemplated such as microwaves and UV-irradiation. It is most likely that all of these factors effect a broad range of damage on DNA, on the precursors of DNA, on the replication and repair of DNA, and on the assembly and maintenance of chromosomes. Dosage ranges for X-rays range from daily doses of 50 to 200 roentgens for prolonged periods of time (3 to 4 wk), to single doses of 2000 to 6000 roentgens. Dosage ranges for radioisotopes vary widely, and depend on the half-life of the isotope, the strength and type of radiation emitted, and the uptake by the cancer or tumor cells.

3. Surgery

Approximately 60% of persons with cancer will undergo surgery of some type, which includes preventative, diagnostic or staging, curative and palliative surgery. Curative surgery is a cancer treatment that may be used in conjunction with other therapies, such as the treatment of the present invention, chemotherapy, radiotherapy, hormonal therapy, gene therapy, immunotherapy and/or alternative therapies.

Curative surgery includes resection in which all or part of cancerous tissue is physically removed, excised, and/or destroyed. Tumor resection refers to physical removal of at least part of a tumor. In addition to tumor resection, treatment by surgery includes laser surgery, cryosurgery, electrosurgery, and microscopically controlled surgery (Mohs' surgery). It is further contemplated that the present invention may be used in conjunction with removal of superficial cancers, precancers, or incidental amounts of normal tissue.

Upon excision of part of all of cancerous cells, tissue, or tumor, a cavity may be formed in the body. Treatment may be accomplished by perfusion, direct injection or local application of the area with an additional anti-cancer therapy. Such treatment may be repeated, for example, every 1, 2, 3, 4, 5, 6, or 7 days, or every 1, 2, 3, 4, and 5 weeks or every 1, 2, 3, 4, 5, 6, 7, 8, 9, 10, 11, or 12 months. These treatments may be of varying dosages as well.

VIII. Examples

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Experimental Procedures

Cell lines and cell culture. All human cell lines used in this study-HEK 293 cells, for development of the recombinant plasmid; MCF-7 breast cancer and MCF-10A normal mammary cells, which are known to have a functional spindle assembly checkpoint; and T47D breast cancer and Ovca432 ovarian cancer cells, which have a defective checkpoint owing to low Mad2 expression were obtained from the American Type Culture Collection (Rockville, Md.). HEK 293 cells, MCF-7 cells, and T47D cells were grown in Dulbecco's modified Eagle's medium (DMEM)/F12 medium. Ovca432 cells were maintained in RPMI 1640. Both DMEM/F12 medium and RPMI 1640 were supplemented with 2 mM L-glutamine, 10% fetal bovine serum (FBS; 100 IU/ml), and penicillin-streptomycin (100 mg/ml). MCF-10A cells were maintained in DMEM/F12 medium supplemented with 5% horse serum, 0.02 μg/ml epidermal growth factor, 0.5 μg/ml hydrocortisone, 10 μg/ml insulin, 0.1 μg/ml cholera toxin, 100 IU/ml penicillin, and 100 mg/ml streptomycin.

Small interfering RNA transfection. Twenty-one-nucleotide siRNA duplexes were synthesized by Dharmacon Research, Inc. (Lafayette, Colo.), to target the Mad2 sequence 5'-AAACCTTTACTCGAGTGCAGA-3' (SEQ ID NO:1) and the BubR1 sequence 5'-AACAATACTCTTCAG-CAGCAG-3' (SEQ ID NO:2). Transfections of MCF-7 cells were performed in accordance with the protocol provided by Dharmacon Research using oligofectamine transfection reagent (Invitrogen, Carlsbad, Calif.). For the control studies, cells were transfected with an siRNA scrambled duplex (Dharmacon Research). The final concentration for the siRNAs was 200 nM.

Production of replication-defective recombinant adenovirus. The adenovirus was produced in accordance with the protocol described previously (He et al., 1998) and Stratagene (La Jolla, Calif.). Briefly, the gene of cDNA Mad2 was first cloned into a shuttle vector, pAdTrack-cytomegalovirus (CMV). The resultant plasmid was linearized by digestion with restriction endonuclease Pme I and subsequently co-transformed into *Escherichia coli* BJ5183 cells using an adenoviral backbone plasmid, pAdEasy-1 (Stratagene, La Jolla, Calif.). Recombinants were selected for kanamycin resistance, and recombination was confirmed by restriction endonuclease analyses. Finally, HEK 293 cells were transfected with the linearized recombinant plasmid. For the study, an infection efficiency of 80-90%, with no cytopathic effect, was obtained in each cell.

Western blot analysis. At 24, 48, and 72 hr after transfection, cells were harvested and subjected to protein immunoblot analysis. Cells were washed once in ice-cold phosphate-buffered saline and lysed with lysis buffer (1% NP-40, 150 mM NaCl, and 50 mM Tris-HCl [pH 7.5]) containing protease inhibitors (1 mM phenylmethane sulphonyl fluoride and 10 μg/ml aprotinin) and phosphatase inhibitors (20 mM β-glycerophosphate, 5 mM NaF, and 100 μM $Na_3VO_4$). After 30 min on ice, cells were subjected to centrifugation at 13,000 rpm for 15 min at 4° C. For Western blotting, equal amounts of proteins were dissolved using sodium dodecyl sulfate-polyacrylamide gel electrophoresis and transferred to nitrocellulose membranes. The membranes were incubated with polyclonal anti-Mad2 antibody (Covance, Princeton, N.J.; 1:500), monoclonal anti-BubR1 antibody (Chemicon, Temecula, Calif.; 1:500), and monoclonal anti-alpha-tubulin (Sigma-Aldrich Chemical Co., St. Louis, Mo.; 1:5000) for 1 hr at room temperature (or overnight at 4° C.), followed by incubation with horseradish peroxidase-conjugated antibodies. The results were visualized with the enhanced chemiluminescence detection system.

Drug sensitivity assays. Cells were detached by trypsinization, seeded at $2.0 \times 10^3$ cells/well in a 96-well microtiter plate, and treated with various concentrations of paclitaxel (1, 5, 10, 50, 100 and 1000 nM). Seventy-two hr later, the effects on cell growth were examined by 3-(4,5-dimethylthiazol-2-yl)-2,5-diphenyl tetrazolium bromide (MTT) assay: 20 μl of MTT solution (5 mg/ml in phosphate-buffered saline; Sigma Aldrich) was added to each well, and the cells were incubated for 4 hr at 37° C. The MTT-formazan formed by metabolically viable cells was dissolved in 100 μl of cell lysis buffer, and fluorescence was monitored using a microplate at a wavelength of 570 nm. The percentage of cell growth was calculated by defining the absorption of cells not treated with paclitaxel (control) as 100%.

Calculation of mitotic indices. Cells with mitotic condensed chromatin were visualized by staining with 10 μM Hoechst 33342 dye (Aventis Pharmaceuticals Inc., Bridgewater, N.J.) in conjunction with 10 μg/ml propidium iodide; the propidium iodide was incorporated into dead cells only. Therefore, dead cells were stained with both propidium iodide and Hoechst 33342 dye, whereas mitotic cells showed the condensed chromatins with Hoechst 33342 dye only. The cells were harvested at 12, 24, and 36 hr after transfection and the mitotic indices calculated.

Cell death analysis. Cell death was evaluated using the trypan blue dye exclusion assay. Briefly, cells were harvested using trypsin and stained with 0.4% trypan blue dye (Sigma-Aldrich Chemical Co., St. Louis, Mo.). Trypan blue-positive and -negative cells were counted using a hemacytometer (Hausser Scientific, Horsham, Pa.) under a phase-contrast microscope (Fisher Scientific, Pittsburgh, Pa.). The results of each assay were expressed in terms of the percentage of dead cells relative to the total number of cells. Individual experiments were performed in triplicate. The results were reported as the mean values±standard deviations.

Cdk1 kinase assay. The Cdk1 protein kinase assay was performed using the SignaTECT cdc2 protein assay system (Promega, Madison, Wis.). Briefly, the harvested cells were lysed with the extraction buffer (50 mM Tris [pH 7.4], 150 mM NaCl, 0.1% Triton X-100, and 1 mM EDTA) containing protease inhibitors (100 μg/ml aprotinin and 0.5 mM phenylmethane sulphonyl fluoride) and phosphatase inhibitors (50 mM NaF). These lysates were conjugated with a substrate consisting of cdc2-specific biotinylated peptide derived from histone H1 and [$\gamma$-$^{32}$P] ATP, and incubated at 30° C. for 10 min. These radiolabeled, phosphorylated substrates were recovered with streptavidin matrix biotin capture membrane (SAM; Promega). After several washings, each captured membrane was placed into a separate vial and analyzed using a liquid scintillation counter (Beckman Coulter, Palo Alto, Calif.).

Preparation of cell lysates for cell cycle profiling. Lysates of the cell lines, subjected to cell cycle profiling, were prepared as follows. The cells were cultivated with DMEM (Dulbeco's Modified Eagle Medium) containing 10% FCS (Fetal Calf Serum), and treated with 100 nM Paclitaxel for 0, 24, 48, or 72 hr. After the treatment, cells were harvested and washed once with PBS. The cells were then lysed with lysis buffer (0.1% NP-40, 20 mM Tris-HCl [pH 7.4], 150 mM NaCl, 2% Proteinase Inhibitor Cocktail [Sigma, St Louis, Mo., USA]) by syringing 20 times with a 21 G needle. After centrifugation at 15000 rpm for 5 min to remove insoluble materials, protein concentration of the supernatant was analyzed (DC Kit, Pierce, Rockford, Ill., USA) and stored at −80° C. until use.

Expression analysis of cell cycle profiling. For the expression analysis of cell cycle profiling, 2.5 μg of total protein was applied to the 78 μl well (3 mm [w]×5 mm [l]×7 mm [d]) of a 5×7 $cm^2$ dot-blot device with a hydrophobic membrane (PVDF with 0.22 μm pores; Millipore, Billerica, Mass., USA). The target protein in the crude sample bound to the membrane was quantitatively detected by sequential reactions with anti-CDK antibodies (Santa Cruz Biotechnology, Santa Cruz, Calif., USA), biotinylated secondary antibody (Santa Cruz Biotechnology), and fluorescein-labeled streptavidin (Vector, Burlingame, Calif., USA). Between each reaction, the well was automatically washed with TBS solution (25 mM Tris-HCl [pH 7.4], 150 mM NaCl). Fluorescent images of the membranes were analyzed using an image analyzer (Bio-Rad, Hercules, Calif., USA), and the intensity of dots quantified using the 'Quantity One' software (Bio-Rad). Relative fluorescence units (RFUs) and the amounts of standard recombinant proteins (Santa Cruz Biotechnology) were linearly correlated in the standardized ranges (CDK1, 2.5-25 ng/dot; CDK2, 1.0-10 ng/dot; CDK4, 1.0-10 ng/dot; CDK6, 2.5-25 ng/dot).

Enzyme activity analyses of cell cycle profiling. Enzyme activity analyses of cell cycle profiling were performed using a non-radioisotopic method. Cell lysates were prepared as described for expression analysis. The CDK molecules were selectively precipitated from 100 μg of lysate total protein with 2 μg of the corresponding antibodies (anti-CDK1, anti-CDK2, anti-CDK4, or anti-CDK6 antibodies; Santa Cruz Biotechnology) and 20 μl of protein A beads (Amersham Pharmacia, Uppsala, Sweden) for 1 hr at 4° C. After three washes with washing buffer (0.1% NP-40, 50 mM Tris-Cl [pH 7.4]), 50 µl of the substrate mixture containing 10 µg of protein substrate, 5 mM adenosine 5'-O-(3-thiotriphosphate) (Sigma), 20 mM Tris-Cl (pH 7.4), and 0.1% Triton X-100 was added to the beads and incubated under continuous shaking at 37° C. for 10 min. Histone H1 (Upstate Biotechnology, Lake Placid, N.Y., USA) was used as the protein substrate for CDK1 and CDK2, and recombinant RB protein (amino acids 769-921) for CDK4 and CDK6. After the beads were removed, the introduced monothiophosphates in the substrate were further labeled by incubation with 10 mM iodoacetyl-biotin (Pierce) in coupling buffer (100 mM Tris-Cl [pH 8.5], 1 mM EDTA) for 90 min in the dark at room temperature. The reaction was quenched with β-mercaptoethanol, and 0.4 µg of the substrate was applied to the wells of the dot-blot device. The wells were blocked with 4% bovine serum albumin (BSA) for 30 min, then incubated with avidin-FITC (Vector) for 1 hr at 37° C. After the membrane had been washed, the images were evaluated using an image analyzer (Bio-Rad), and the fluorescence intensity of the dots was quantified using the 'Quantity One' software (Bio-Rad). The activity was calculated with a standard curve prepared with CDK activities corresponding to 0, 12.5, 25, 50, 100, and 150 µg of protein extracted from a K562 chronic myelogenous leukemia cell line. One unit (U) is equivalent to the kinase activity of 1 µg of total protein from the K562 cells.

Example 2

Inactivation of Spindle Assembly Checkpoint and Correlation with Suppression of Cdk1 Activity Previous studies have shown that upon activation of the spindle assembly checkpoint, both Mad2 and BubR1 interact with Cdc20 directly and inhibit its ability to activate APC (Fang et al., 1998; Sudakin et al., 2001; Tang et al., 2001; Fang, 2002). To determine whether suppression of Mad2 or BubR1 through transient knockdown in cell lines would affect the function of the spindle assembly checkpoint induced by paclitaxel, we performed gene silencing using siRNA duplexes.

Transfection of MCF-7 cells, which have a functional checkpoint, with the 21-nucleotide small interfering RNA (siRNA) duplex homologous to a portion of the Mad2 and BubR1 sequences resulted in dramatic reduction of Mad2 and BubR1 protein levels; these levels remained low at 24, 48, and 72 hr after transfection in each cell line. Co-transfection of MCF-7 cells with siRNA/Mad2 and siRNA/BubR1 also reduced both expressions, yielding results similar to those obtained with single transfection (FIG. 1A). The scrambled siRNA duplex (siRNA/control) did not affect the expression level of Mad2 or BubR1, verifying the specificity of the siRNA approach.

Figure 1B:
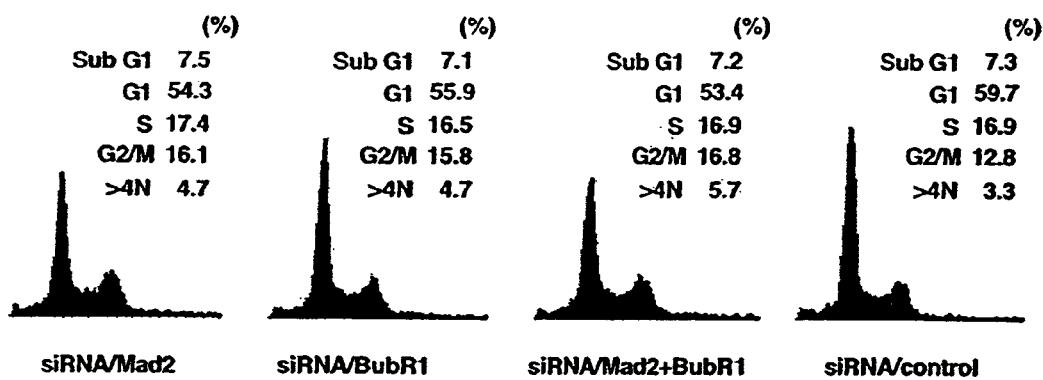
Figure 1C:
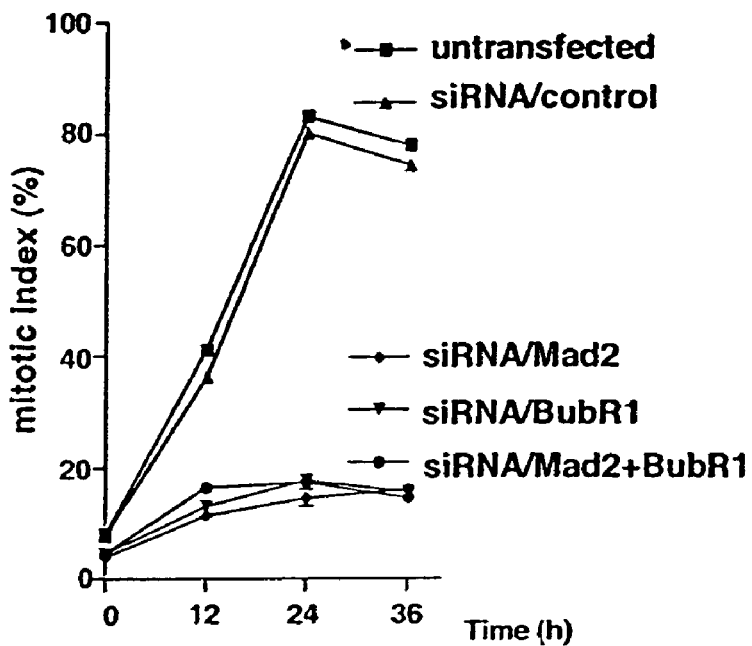
Figure 1D:
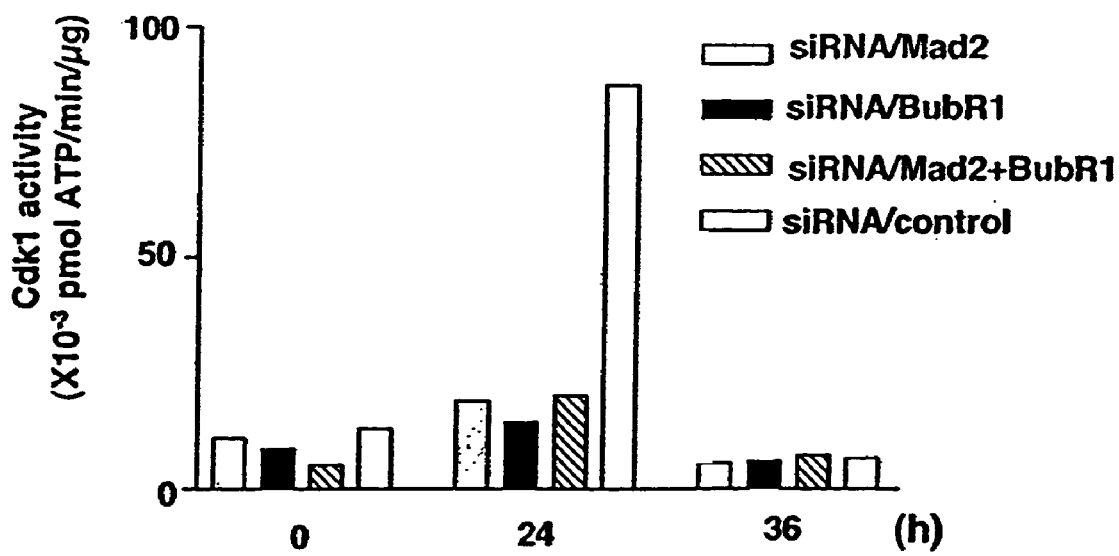

Using flow cytometry, the inventors attempted to rule out the possibility that transient suppression of mitotic checkpoint genes does not affect the cell cycle distribution. Seventy-two hr after transfection, cell cycle distributions in both the Mad2- and the BubR1-suppressed cells were similar to the distributions in control cells (FIG. 1B). To test the effects of suppression of Mad2, BubR1, or both on the spindle assembly checkpoint activated by paclitaxel, the mitotic indices were determined and the Cdk1 activity measured, both of which reflect the status of this checkpoint. Twenty-four hr after paclitaxel treatment, at least 80% of the control cells were arrested at mitosis and showed a dramatic increase in Cdk1 activity, thus verifying activation of the spindle assembly checkpoints (FIG. 1C and FIG. 1D). In contrast, the accumulation of mitotic indices and activation of Cdk1 were incomplete in Mad2- and BubR1-suppressed cells (FIG. 1C and FIG. 1D). Interestingly, concurrent suppression of Mad2 and BubR1 showed loss of accumulation of mitotic indices and activation of Cdk1, results similar to those obtained with suppression of either Mad2 or BubR1 alone (FIG. 1C and FIG. 1D). These results indicate that Mad2 or BubR1 alone was sufficient to abolish the function of the spindle assembly checkpoint. This abolishment was reflected by suppression of Cdk1 activity.

Recent reports have clearly demonstrated that every single spindle assembly checkpoint gene thus far identified is essential for maintaining mitotic arrest Dobles et al., 2000; Kalitsis et al., 2000; Luo et al., 2002). Mad2 and BubR1 act cooperatively in the mitotic checkpoint complex for the initiation and maintenance of the spindle assembly checkpoint (Fang, 2002), a finding that appears consistent with the present results. Moreover, in previous studies, transfection of MDA-MB-231 and SKBr-3 cells, which have a functional spindle assembly checkpoint, with siRNA/Mad2, siRNA/BubR1, or both; resulted in loss of the checkpoint and resistance to paclitaxel (data not shown). These cell lines are known to have mutated p53 and HER2/neu overexpression respectively. Despite these known genetic differences, abolishment of the spindle assembly checkpoint conferred similar findings of resistance to paclitaxel.

Example 3

Loss of Spindle Assembly Checkpoint and Paclitaxel Resistance

Figure 2A:
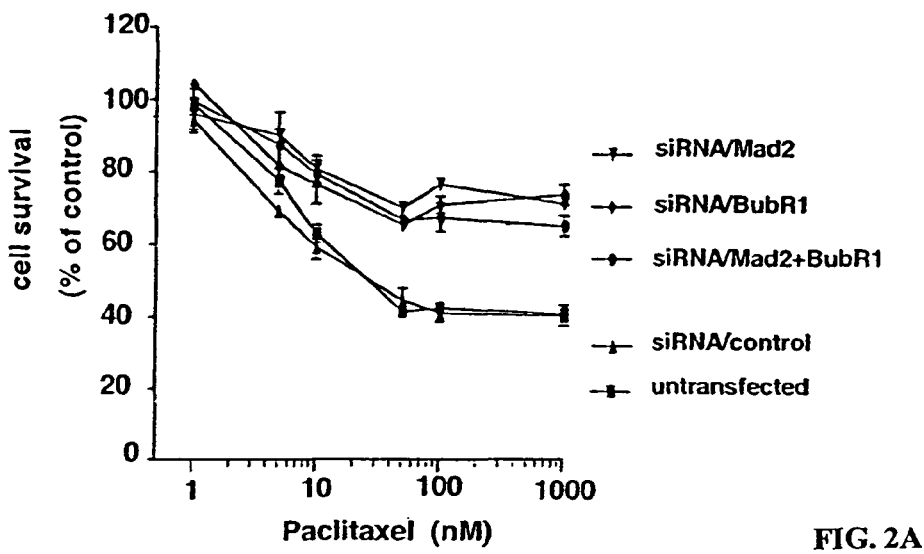
FIGS. 2A-2B. Induction of paclitaxel resistance via loss of spindle assembly checkpoint.
Figure 2B:
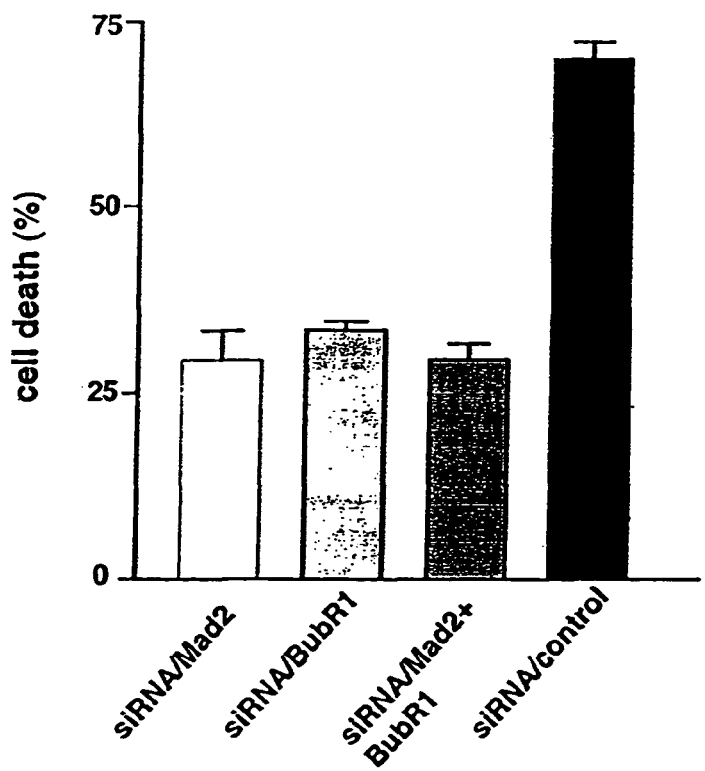

To determine the effect of loss of spindle assembly checkpoint due to suppression of Mad2, BubR1, or both on paclitaxel sensitivity, the cell viability of paclitaxel using the MTT assay was compared. As shown in FIG. 2A, MCF-7 cells in which Mad2, BubR1, or both were suppressed, were more resistant to paclitaxel than control cells. Next, to determine whether these resistances were due to the reduction of cell death induced by paclitaxel, the inventors assessed the population of cell death using trypan blue exclusion. Forty-eight hr after treatment with paclitaxel, levels of cell death were high in control cells but reduced in the cells in which Mad2, BubR1, or both were suppressed (FIG. 2B). These data demonstrate that loss of the spindle assembly checkpoint increases paclitaxel resistance.

Example 4

Figure 3A:
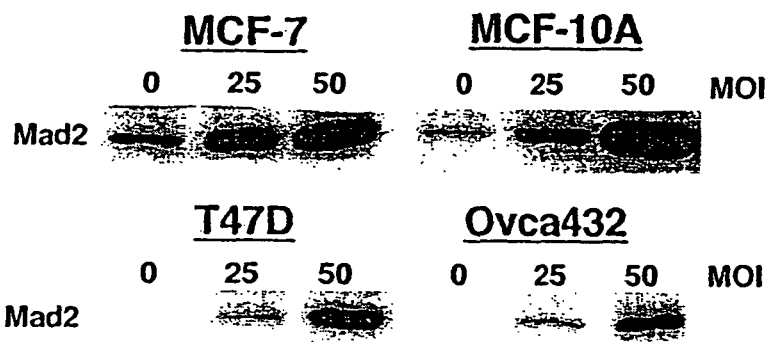
FIGS. 3A-3G. Restoration of function of spindle assembly checkpoint and enhancement of paclitaxel sensitivity by overexpression of Mad2 in Mad2-dependent checkpoint-defective cells.
Figure 3B:
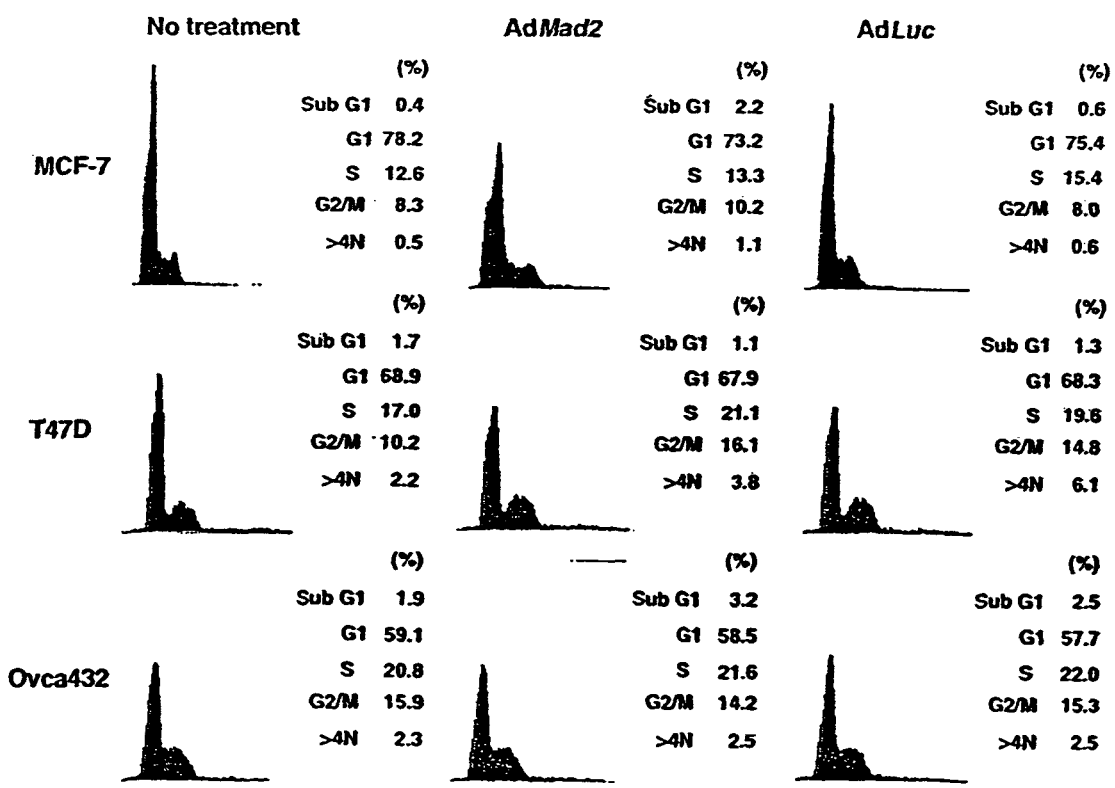

Effect of Mad2 Overexpression on Cdk1 Activity and Paclitaxel Sensitivity in Mad2-Dependent, Checkpoint-Defective Cells Although Mad2 mutations have not been detected in cancer cell lines with checkpoint defects (Takahashi et al., 1999), the expression level of Mad2 protein appears to correlate with the competence of the spindle assembly checkpoint (Wang et al., 2000; Wang et al., 2002). Few reports on the expression level of Mad2 protein in human specimens have been published (Tanaka et al., 2001). Therefore, it was determined whether overexpression of Mad2 restores spindle assembly checkpoint activation in cells in which low Mad2 expression renders the spindle assembly checkpoint nonfunctional. To express Mad2 effectively, the recombinant adenovirus that expresses Mad2 (Ad-EGFP/Mad2) was generated. This adenovirus contains 2 independent CMV-driven transcription units (1 for GFP and 1 for Mad2), allowing direct observation of the efficiency of infection. Ad-EGFP/Mad2 induced high expression of exogenous Mad2 (FIG. 3A) and did not affect the distribution of cells among the various phases of the cell cycle (FIG. 3B).

Figure 3C:
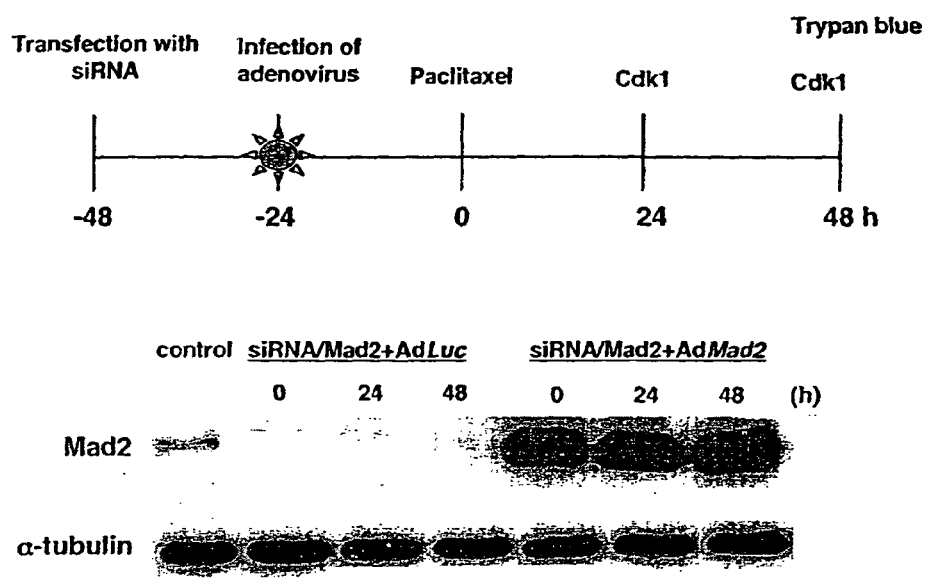
Figure 3D:
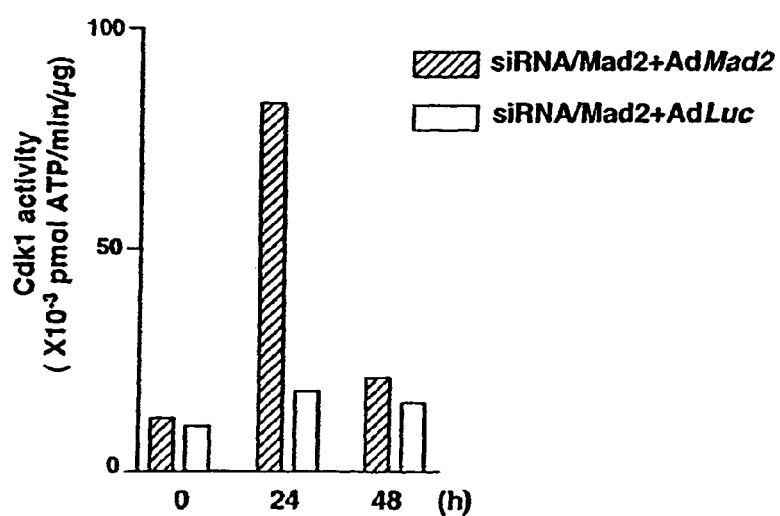
Figure 3E:
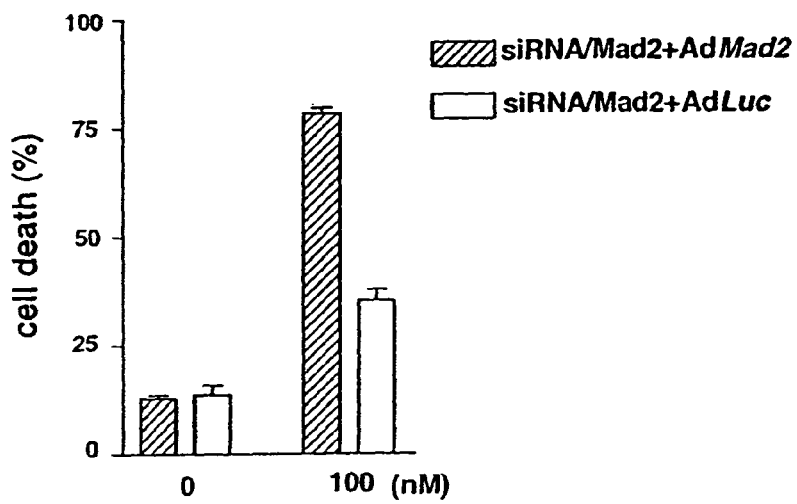

First, Mad2-knockdown MCF-7 cells, which were shown to have a nonfunctional checkpoint were employed (FIG. 1C and FIG. 1D). The expression of Mad2 was restored in Mad2-knockdown cells by infection of Ad-EGFP/Mad2 (FIG. 3C). Then, to determine whether the function of the checkpoint can be restored by re-expression of Mad2, the activation of Cdk1 in Ad-EGFP/Mad2-infected Mad2-knockdown cells was assessed after paclitaxel treatment. The Cdk1 activity did not increase in the cells that had been infected with recombinant adenovirus, which expressed luciferase (Ad-EGFP/Luc) even after exposure to paclitaxel; these findings are consistent with the data presented in FIG. 1. In contrast, Cdk1 activity was restored in the Ad-EGFP/Mad2-infected cells, indicating that overexpression of Mad2 can restore the function of the spindle assembly checkpoint (FIG. 3D). It was next determined whether this restoration enhanced the level of cell death induced by paclitaxel and found that paclitaxel-induced cell death was, indeed, significantly higher in the Ad-EGFP/Mad2-infected cells than in the Ad-EGFP/Luc-infected cells (FIG. 3E).

Figure 3F:
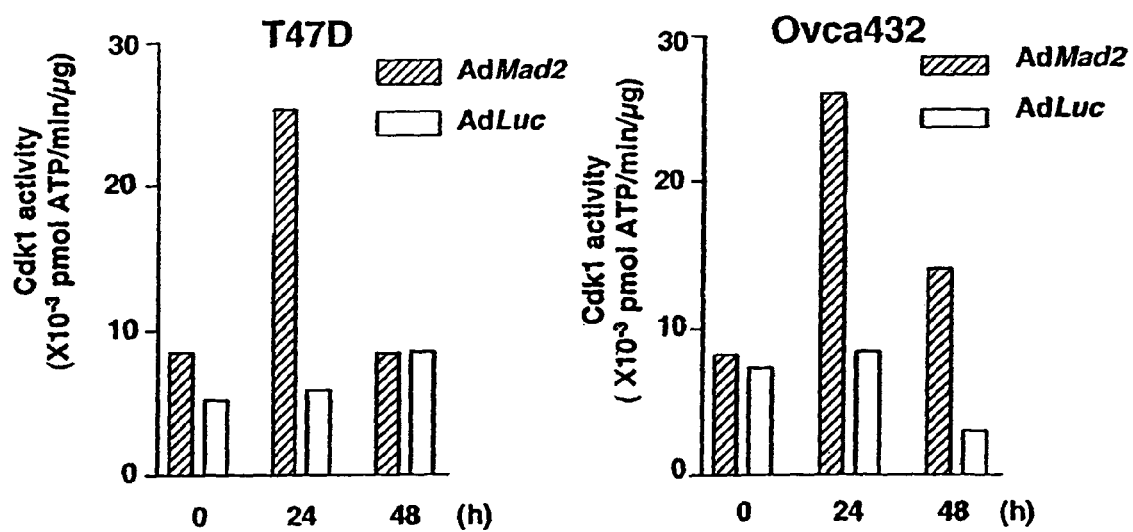
Figure 3G:
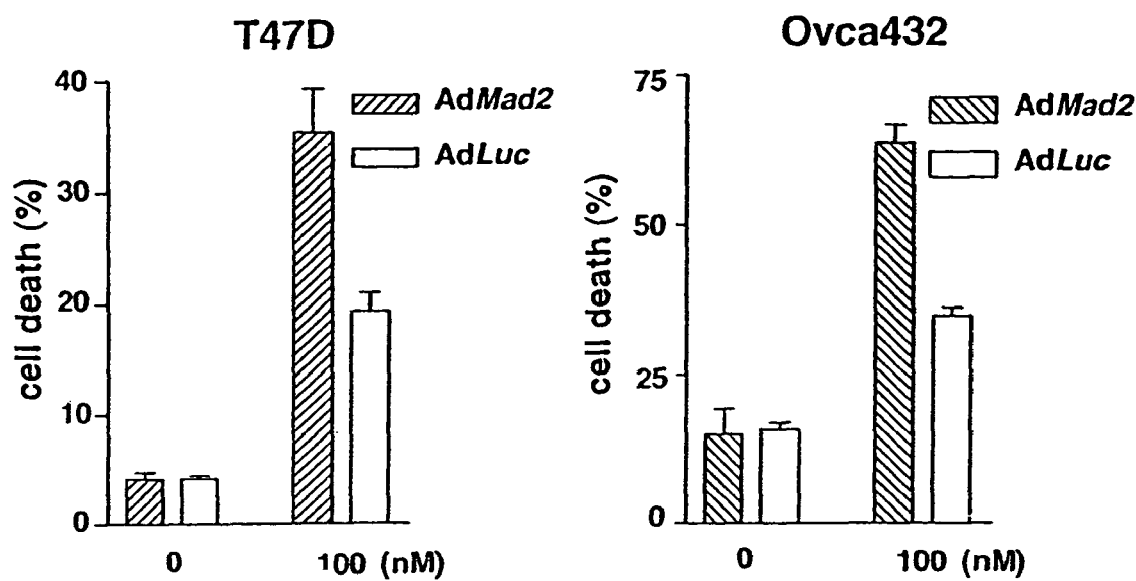

T47D and Ovca432 cells, which are known to show the defective checkpoint owing to low expression of Mad2 were also employed (Li and Benezra, 1996). Infection of these cell lines with Ad-EGFP/Mad2 induced high expression levels of exogenous Mad2 and did not affect the cell cycle distribution (FIG. 3A and FIG. 3B). The Cdk1 activity and paclitaxel sensitivity were higher in the Ad-EGFP/Mad2-infected cells than in the Ad-Luc-infected cells (FIG. 3F and FIG. 3G). Thus, these data demonstrate that exogenous Mad2 expression can restore the function of the checkpoint and enhance cell death in Mad2-dependent checkpoint-defective cells.

Example 5

Figure 4A:
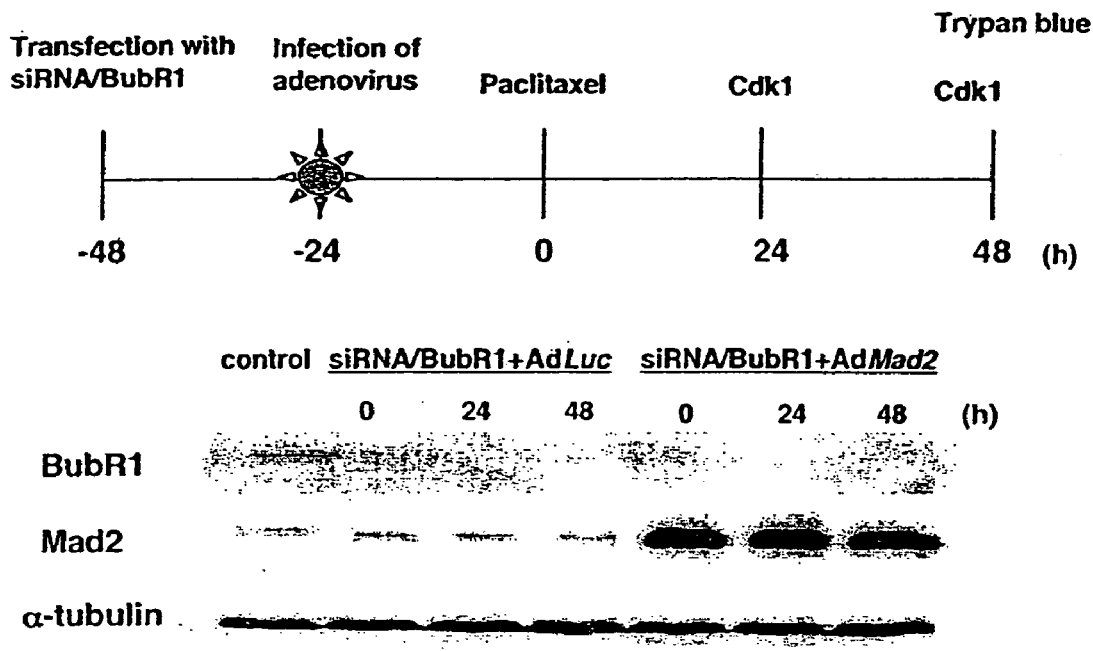
FIGS. 4A-4E. Inability of Mad2 overexpression to enhance checkpoint function and paclitaxel sensitivity in cells with Mad2-independent defective or functional checkpoint.
Figure 4B:
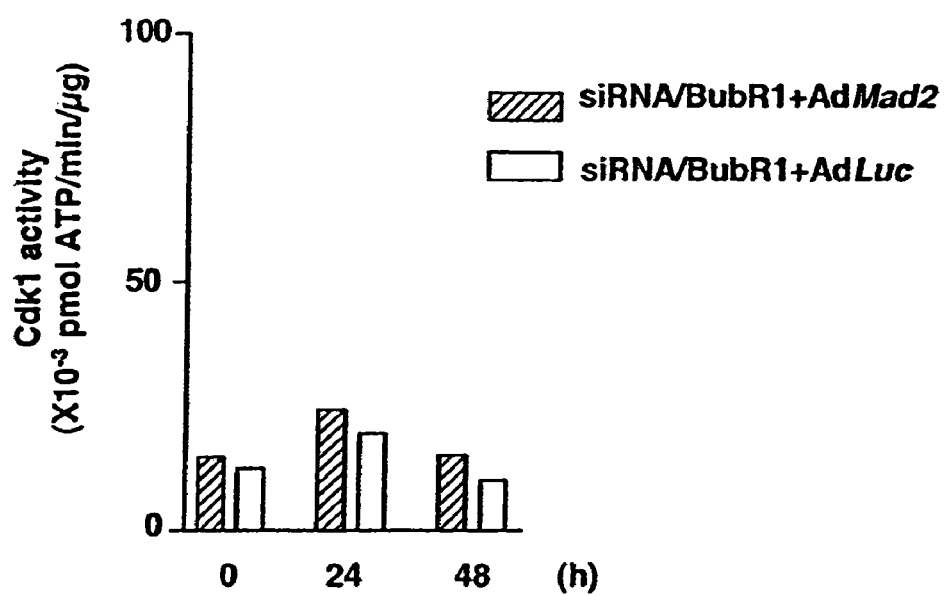
Figure 4C:
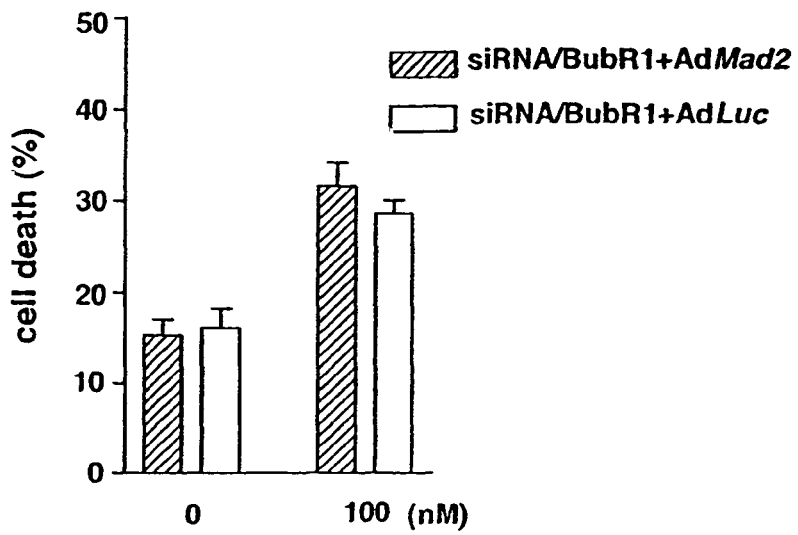

Effect of Mad2 Overexpression on Checkpoint Function and Paclitaxel Sensitivity in Bubr1-Suppressed Cells It was next determined whether overexpression of Mad2 could overcome spindle assembly checkpoint defects due to molecules other than Mad2. BubR1-knockdown MCF-7 cells, which were shown to be defective at the checkpoint were employed (FIG. 1C and FIG. 1D). Ad-EGFP/Mad2 induced high expression of exogenous Mad2 and did not affect the expression of BubR1 in BubR1-knockdown cells (FIG. 4A). However, Cdk1 was not up-regulated in Ad-EGFP/Mad2-infected cells, and paclitaxel-induced cell death was not enhanced (FIG. 4B and FIG. 4C). These data indicate that overexpression of Mad2 did not overcome the function of the checkpoint and paclitaxel sensitivity in cells with a Mad2-independent defective checkpoint.

Example 6

Effect of Overexpression of Mad2 on Checkpoint Function and Paclitaxel Sensitivity in Cells with Functional Checkpoint Next, it was determined whether overexpression of Mad2 enhances the function of the spindle assembly checkpoint (Cdk1 activity and paclitaxel sensitivity), a finding that could translate into enhanced paclitaxel-induced cell death in checkpoint-intact cells. Previous reports have shown that deletion of one Mad2 allele results in a defective spindle assembly checkpoint (Michel et al., 2001) and that Mad2 must be recruited to the kinetochores via its interaction with Mad1 and inhibition of APC/Cdc20 (Chen et al., 1998; Waters et al., 1998). These results suggest that a certain quantity and a specific localization of Mad2 are required for Mad2 to act as a component in the spindle assembly checkpoint machinery and that large quantities of Mad2 may not be necessary for enhancement of the function of the checkpoint.

Figure 4D:
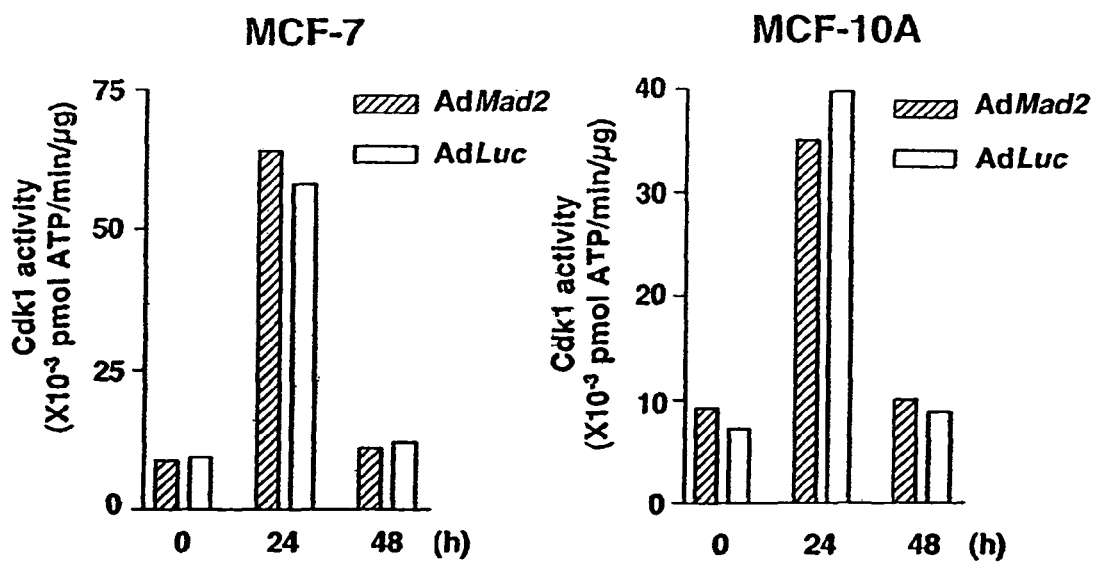
Figure 4E:
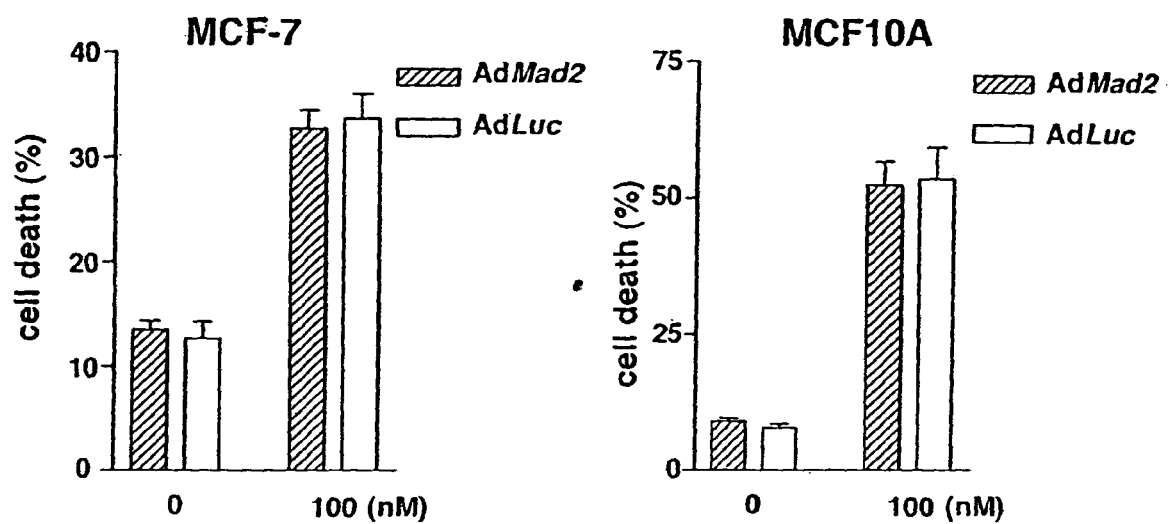

In MCF-10A cells and MCF-7 cells, both of which are known to have a functional checkpoint, Ad-EGFP/Mad2 effectively induced high expression levels of Mad2 (FIG. 3A). However, Cdk1 activity was not increased in Ad-EGFP/Mad2-infected cells of either cell line and therefore no enhancement of paclitaxel-induced cell death (FIG. 4D and FIG. 4E). Thus, overexpression of Mad2 failed to enhance the checkpoint functionality and paclitaxel sensitivity in cells with a basically functional spindle assembly checkpoint.

Because losses or gains of chromosomes are hallmarks in human cancers, it is suspected that the spindle assembly checkpoint is frequently lost in the clinical setting. Despite many reports of detection of spindle assembly checkpoint defects in human lung, colorectal, ovarian, and nasopharyngeal cancer cell lines in vitro (Takahashi et al., 1999; Wang et al., 2000; Cahill et al., 1998; Nakagawa et al., 2002; Saeki et al., 2002), mutations in known spindle assembly checkpoint genes occur very rarely in human cancers (Saeki et al., 2002; Sato et al., 2000; Haruki et al., 2001). This paradox may be explained by various post-transcriptional or post-translational modifications to checkpoint complexes. Moreover, because the spindle assembly checkpoint machinery consists of various molecules, assessing the function of the checkpoint in human cancer samples by analyzing mutations of genes or protein expressions would be impractical.

Example 7

Sensitivities of the Cell Lines to Paclitaxel

Figure 5:
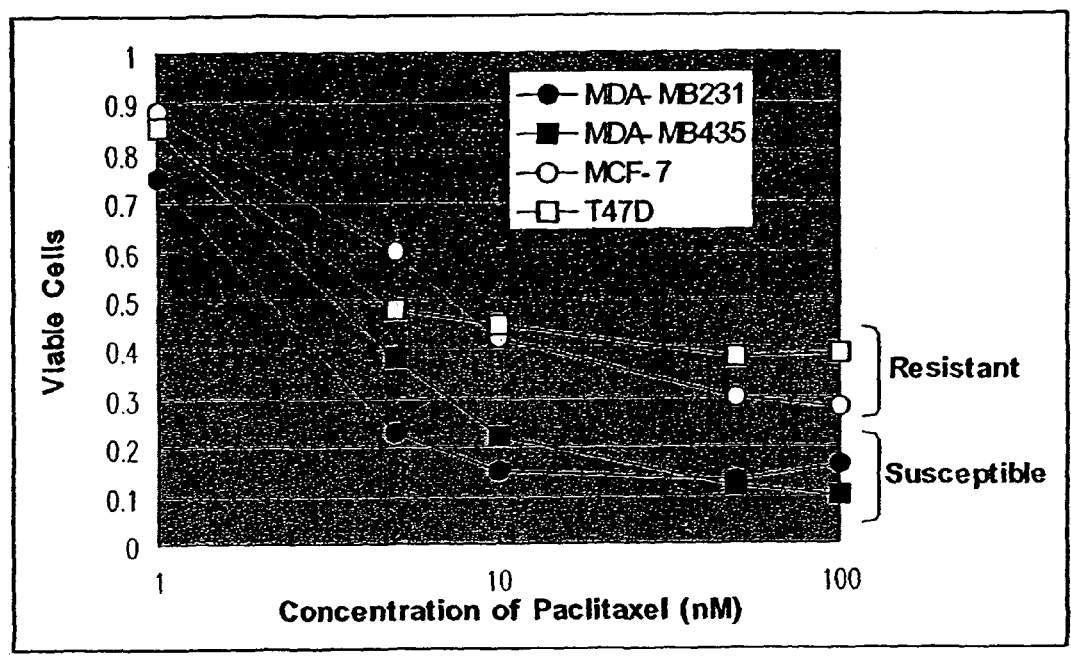
FIG. 5. Sensitivities of cell lines to Paclitaxel were judged according to a graph analysis of the Paclitaxel cytotoxicity test. In the results, MDA-MB231 and MDA-MB435 were judged as susceptible, and MCF-7 and T47D were judged as resistant. The Paclitaxel cytotoxicity test was performed as follows. The cells were cultivated in wells of a 96-well culture plate in presence of 1, 5, 10, 50 or 100 nM Paclitaxel. After 72 hr cultivation, cell survival was measured by the MTT assay.

Sensitivities of four human breast cancer cell lines to paclitaxel were judged according to a graph analysis of the paclitaxel cytotoxicity test (FIG. 5). The results showed that MDA-MB231 and MDA-MB435 were susceptible, and MCF-7 and T47D were resistant. The paclitaxel cytotoxicity test was performed as follows. The cells were cultivated in wells of a 96-well culture plate in presence of 1, 5, 10, 50 or 100 nM paclitaxel. After 72 hr cultivation, cell survival was measured by the MTT assay.

Example 8

In Vitro Validation

Figure 6:
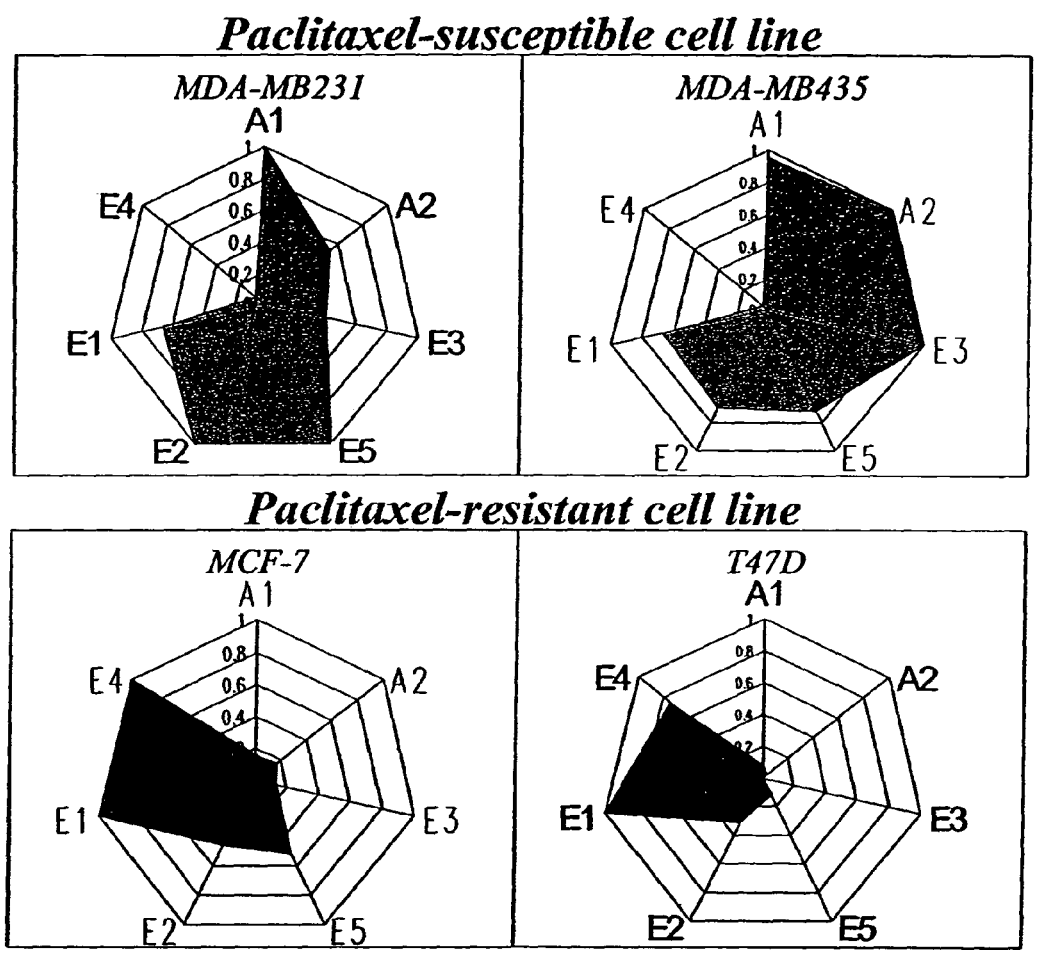
FIG. 6. Lysates of the cell lines were subjected to cell cycle profiling. The cell cycle profiling technology revealed that seven parameters were useful for differentiating susceptible and resistant cell lines. These are (A1) CDK1 specific activity 24 hr after treatment; (A2) CDK2 specific activity before treatment; (E5) MAD2 expression before treatment; (E2) Cyclin B1 before treatment; (E3) Cyclin E expression before treatment; (E4) p21 expression before treatment; and (E1) CDK6 expression before treatment. The value plotted in the graph was calculated by dividing with the biggest raw value among the four cell lines on the each parameter. For example, raw values of cyclin B1 expression (E2, ng/μg of lysate); 0.135 for MDA-MB231, 0.094 for MDA-MB435, 0.061 for MCF-7, and 0.042 for T47D, became 1.0 for MDA-MB231, 0.70 for MDA-MB435, 0.45 for MCF-7, and 0.31 for T47D by dividing with 0.135 of MDA-MB231.

In an in vitro validation study, all cell lines were treated with 100 nM paclitaxel and harvested at 0, 24, 48, and 72 hr after the treatment. Then, the cell lysates were subjected to cell cycle profiling. The profiling results revealed that seven parameters (cell cycle molecules) are useful for differentiating susceptible and resistant cell lines to paclitaxel. These are (1) CDK1 specific activity 24 hr after treatment; (2) CDK2 specific activity before treatment; (3) MAD2 expression before treatment; (4) Cyclin B1 before treatment; (5) Cyclin E expression before treatment; (6) p21 expression before treatment; and (7) CDK6 expression before treatment (FIG. 6). According to the results, nine parameters were determined for the paclitaxel sensitivity prediction test. These are (1) CDK1 kinase activity; (2) CDK1 expression (for calculation of CDK1 specific activity); (3) CDK2 kinase activity; (4) CDK2 expression (for calculation of CDK2 specific activity); (5) MAD2 expression; (6) Cyclin B1; (7) Cyclin E expression; (8) p21 expression; and (9) CDK6 expression.

The cell cycle profiling technology revealed that seven parameters were useful for differentiating susceptible and resistant cell lines. These are (1) CDK1 specific activity 24 hr after treatment; (2) CDK2 specific activity before treatment; (3) MAD2 expression before treatment; (4) Cyclin B1 before treatment; (5) Cyclin E expression before treatment; (6) p21 expression before treatment; and (7) CDK6 expression before treatment (FIG. 6).

Example 9

In Vivo Validation

Figure 7:
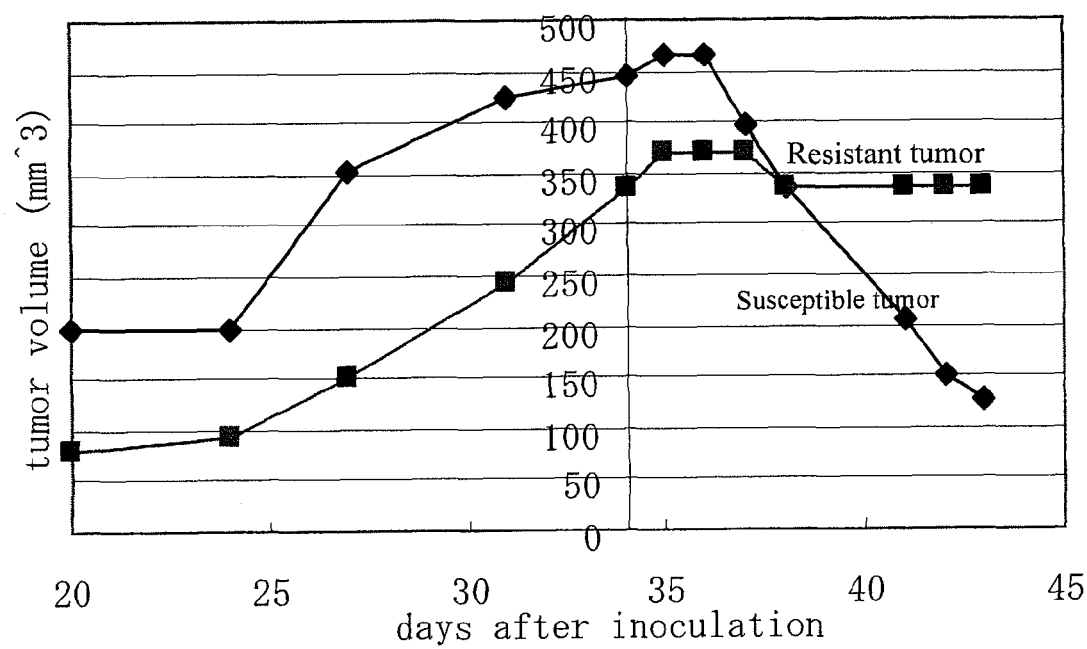
FIG. 7. The susceptible and resistant cells ($1\times10^7$ cells/mouse) were inoculated into nude mice. When the tumor volume reached more than 300 mm$^3$, 20 mg of Paclitaxel per day was intraperitoneally administered on five consecutive days (Days 34-38 after the inoculations). The tumor size was recorded on Days 20-43.

To further confirm the above in vitro results, an in vivo validation study was performed. The susceptible and resistant cells were inoculated into nude mice. When the tumor volume reached more than 300 mm$^3$, 20 mg of paclitaxel per day was intraperitoneally administered on five consecutive days (Days 34-38 after the inoculations). The tumor size was recorded on days 20-43. As shown in FIG. 7, susceptible tumors showed a significant decrease in tumor volume, from 460 mm$^3$ to 120 mm$^3$. By contrast, volume of resistant tumors remained at 350 mm$^3$ until day 43.

Figure 8:
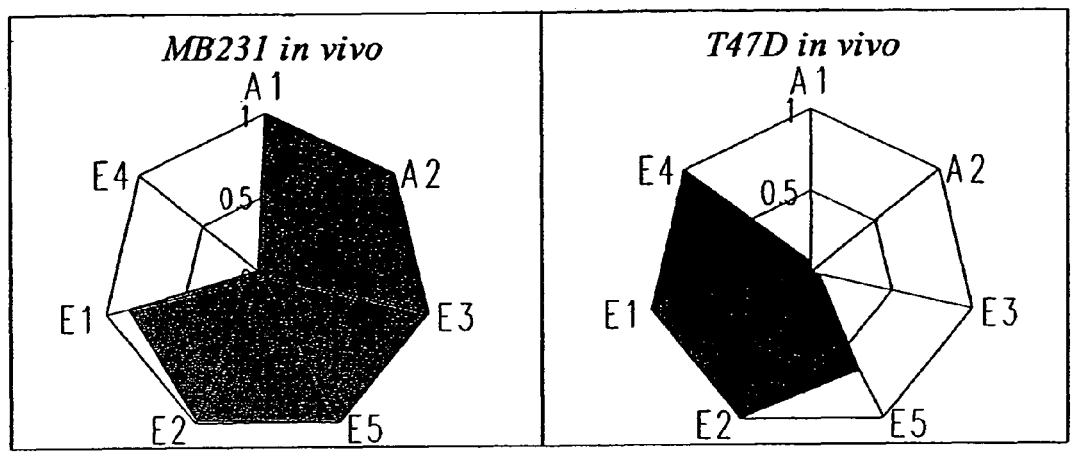
FIG. 8. Lysates of the tumor tissues from tumor-bearing mice were subjected to cell cycle profiling. The cell cycle technology showed almost identical results as in vitro studies except for cyclin B1 expression (E2). Six parameters were useful for differentiating susceptible and resistant tumors. These are (A1) CDK1 specific activity 24 hr after treatment; (A2) CDK2 specific activity before treatment; (E5) MAD2 expression before treatment; (E3) Cyclin E expression before treatment; (E4) p21 expression before treatment; and (E1) CDK6 expression before treatment. The value plotted in the graph was calculated by dividing with the bigger raw value between two tumors on the each parameter. For example, raw values of CDK1 specific activity (A1, mU/ng of CDK1); 3.0 for tumor of MDA-MB231, and 0.2 for tumor of T47D, became 1.0 for MDA-MB231 and 0.067 for T47D.

The tumor tissues were surgically dissected from tumor-bearing mice before and after 24 hr of paclitaxel administration, and subjected to cell cycle profiling. The profiling showed almost identical results as the in vitro studies, except for cyclin B1 expression. Six parameters were useful for differentiating susceptible and resistant tumor to paclitaxel. These are (1) CDK1 specific activity 24 hr after treatment; (2) CDK2 specific activity before treatment; (3) MAD2 expression before treatment; (4) Cyclin E expression before treatment; (5) p21 expression before treatment; and (6) CDK6 expression before treatment (FIG. 8).

Combining the results of the in vitro and in vivo validation studies, the cell cycle profiling technology has proven to be a valid system for determining Taxane chemosensitivity in tumor tissue. The selected parameters for the determination are scientifically proven to generate an accurate prediction.

The above results strongly indicate that the cell cycle profiling technology is successful in determining the Taxane chemosensitivity of tumor tissue. Combining the results of the in vitro and in vivo validation studies, the cell cycle profiling technology has proven to be successful in determining the Taxane chemosensitivity of tumor tissue.

Example 10

Sensitivity to Paclitaxel in Nude Mice

The susceptible and resistant cells (1×10$^7$ cells/mouse) were inoculated into nude mice. When the tumor volume reached more than 300 mm$^3$, 20 mg of paclitaxel per day was intraperitoneally administered on five consecutive days (Days 34-38 after the inoculations). The tumor size was recorded on days 20-43. As shown in FIG. 7, susceptible tumor showed a dramatic decrease in tumor volume from 460 mm$^3$ to 120 mm$^3$. By contrast, the volume of resistant tumor remained at 350 mm$^3$ until day 43 (FIG. 7).

For cell cycle profiling, the tumor tissues were surgically dissected from tumor-bearing mice before and after 24 hr of Paclitaxel administration. Lysates of pieces (2 mm$^3$) of the tissues were prepared using a tissue-homogenizer with lysis buffer (0.1% NP-40, 20 mM Tris-HCl [pH 7.4], 150 mM NaCl, 2% Proteinase Inhibitor Cocktail (Sigma, St Louis, Mo.)). The homogenizer removes insoluble materials automatically on a filter disk. Protein concentration of the lysate was analyzed (DC Kit, Pierce, Rockford, Ill., USA) and stored at −80° C. until use.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and methods and in the steps or in the sequence of steps of the methods described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

U.S. Pat. No. 4,814,470
U.S. Pat. No. 4,857,653
U.S. Pat. No. 4,942,184
U.S. Pat. No. 4,960,790
U.S. Pat. No. 5,059,699
U.S. Pat. No. 5,157,049
U.S. Pat. No. 5,200,534
U.S. Pat. No. 5,202,448
U.S. Pat. No. 5,229,529
U.S. Pat. No. 5,248,796
U.S. Pat. No. 5,254,580
U.S. Pat. No. 5,272,171
U.S. Pat. No. 5,274,137
U.S. Pat. No. 5,278,324
U.S. Pat. No. 5,279,949
U.S. Pat. No. 5,283,253
U.S. Pat. No. 5,294,637
U.S. Pat. No. 5,300,638
U.S. Pat. No. 5,350,866
U.S. Pat. No. 5,352,805
U.S. Pat. No. 5,362,831
U.S. Pat. No. 5,380,751
U.S. Pat. No. 5,395,850
U.S. Pat. No. 5,399,363
U.S. Pat. No. 5,403,858
U.S. Pat. No. 5,407,683
U.S. Pat. No. 5,411,984
U.S. Pat. No. 5,412,092
U.S. Pat. No. 5,415,869
U.S. Pat. No. 5,422,364
U.S. Pat. No. 5,424,073
U.S. Pat. No. 5,433,364
U.S. Pat. No. 5,438,072
U.S. Pat. No. 5,440,056
U.S. Pat. No. 5,641,803
U.S. Pat. No. 5,646,176
U.S. Pat. No. 5,665,671
U.S. Pat. No. 5,698,712

U.S. Pat. No. 5,705,503
U.S. Pat. No. 5,728,687
U.S. Pat. No. 5,739,539
U.S. Pat. No. 5,773,464
U.S. Pat. No. 5,821,263
U.S. Pat. No. 5,840,929
U.S. Pat. No. 5,912,264
U.S. Pat. No. 5,977,376
U.S. Pat. No. 6,017,935
U.S. Pat. No. 6,284,746
U.S. Pat. No. 6,362,217
U.S. patent application Ser. No. 10/423,892
U.S. Patent Pub. 2002/0164673
U.S. Patent Pub. 20020016356
U.S. Patent Pub. 2003/0124055
U.S. Patent Pub. 2003/0130170
U.S. Patent Pub. 2003/0130178
U.S. Patent Pub. 2003/0130341
U.S. Patent Pub. 2003/0134793
U.S. Patent Pub. 2003/0144344
U.S. Patent Pub. 2003/0147807
European Appln. EP 590267
PCT Appln. WO 95/33740
PCT Appln. WO 95/33736
PCT Appln. WO 93/24476
PCT Appln. WO 93/23555
PCT Appln. WO 94/20089
PCT Appln. WO 94/15929
PCT Appln. WO 94/15599
PCT Appln. WO 93/10076
PCT Appln. WO 94/07882
PCT Appln. WO 94/07881
PCT Appln. WO 94/07880
PCT Appln. WO 94/07876
PCT Appln. WO 96/03394
PCT Appln. WO 93/02067
PCT Appln. WO 96/00724
PCT Appln. WO 94/00156
Arap et al., *Cancer Res.*, 55(6):1351-1354, 1995.
Bishop et al., *J. Clin. Oncol.*, 17:2355-2364, 1999.
Cahill et al., *Nature*, 392:300-303, 1998.
Caldas et al., *Nat. Genet.*, 8(1):27-32, 1994.
Chan et al., *J. Cell Biol.*, 146:941-954, 1999.
Chen et al., *J. Cell Biol.*, 143:283-295, 1998.
Cheng et al., *Cancer Res.*, 54(21):5547-5551, 1994.
Dobles et al., *Cell*, 101:635-645, 2000.
Eifel et al., *J. Natl. Cancer Inst.*, 93(13):979-989, 2001.
Fang et al., *Anticancer Res.*, 20(1A):103-111, 2000.
Fang et al., *Genes Dev.*, 12:1871-1883, 1998.
Fang et al., *Neuron*, 28:183-193, 2000.
Fang, *Mol. Biol. Cell*, 13:755-766, 2002.
Fuchs and Johnson, *Cancer Treat Rep.*, 1219-1222, 1978.
Gatzemeier et al., *Lung Cancer*, 12:S101-S106, 1995.
Giannakakou et al., *J. Biol. Chem.*, 272:17118-17125, 1997.
Gotaskie and Andreassi, *Cancer Pract.*, 2:27-33, 1994.
Guchelaar et al., *Clinical Oncology—R-Coll. Radiology*, 6:40-48, 1994.
Haruki et al., *Cancer Lett.*, 162:201-205, 2001.
He et al., *Proc. Natl. Acad. Sci. USA*, 95:2509-2514, 1998.
Holmes et al., *J. Natl. Cancer Institute*, 83:1797-1805, 1991.
Horwitz et al., *Cold Spring Harb. Symp. Quant. Biol.*, 46(1):219-226, 1982.
Huang et al., *Apoptosis*, 2000 µm; 5(3): 235-241, 2000.
Huang et al., *Carcinogenesis*, 18:83-88, 1997.
Huang et al., *Nat. Struct. Biol.*, 7:634-638, 2000.
Huizing et al., *Cancer Invest.*, 13(4):381-404, 1995.
Hussussian et al., *Nat. Genet.*, 8(1):15-21, 1994.
Jin et al., *Cell*, 93:81-91, 1998.
JP Patent Application 200348653
Kalitsis et al., *Genes Dev.*, 14:2277-2282, 2000.
Kamb et al., *Nat. Genet.*, 8(1):23-26, 1994a
Kamb et al., *Science*, 2674:436-440, 1994b.
Li and Benezra, *Science*, 274:246-248, 1996.
Long and Fairchild, *Cancer Research*, 54:4355-4361, 1994.
Luo et al., *Mol. Cell*, 9:59-71, 2002.
McGuire et al., *N. Engl. J. Med.*, 334:1-6, 1996.
Meikrantz and Schlegel, *J. Biol. Chem.*, 271:10205-10209, 1996.
Michel et al., *Nature*, 409:355-359, 2001.
Mori et al., *Cancer Res.*, 54(13):3396-3397, 1994.
Nabholtz et al., *J. Clin. Oncol.*, 14(6):1858-1867, 1996.
Nakagawa et al., *Oncol. Rep.*, 9:1229-1232, 2002.
Nigg, *Nat. Rev. Mol. Cell. Biol.*, 2:21-32, 2001.
Nobri et al., *Nature (London)*, 368:753-756, 1995.
Okamoto et al., *Proc. Natl. Acad. Sci. USA*, 91(23):11045-11049, 1994.
Orlow et al., *Cancer Res*, 54(11):2848-2851, 1994.
Pazdur et al., *Cancer Treat. Rev.*, 19(4):351-386, 1993.
Piccart et al., *J. Natl. Cancer Institute*, 92:699-708, 2000.
Remington's Pharmaceutical Sciences, 15$^{th}$ ed., pages 1035-1038 and 1570-1580, Mack Publishing Company, Easton, Pa., 1980.
Ringel and Horwitz, *J. Natl. Cancer Inst.*, 83(4):288-291, 1991.
Saeki et al., *Cancer*, 94:2047-2054, 2002.
Sato et al., *Jpn. J. Cancer Res.*, 91:504-509, 2000.
Schiff et al., *Nature*, 277:665-667, 1979.
Serrano et al., *Nature*, 366:704-707, 1993.
Serrano et al., *Science*, 267(5195):249-252, 1995.
Shen et al., *Cell Growth Differ.*, 9:23-29, 1998.
Smith et al., *Semin. Oncology*, 22:41-46, 1995.
Sudakin et al., *J. Cell Biol.*, 154:925-936, 2001.
Takahashi et al., *Oncogene*, 18:4295-4300, 1999.
Tan et al., *Mol. Cell*, 9(5):993-1004, 2002.
Tanaka et al., *Jpn. J. Cancer Res.*, 92:952-958, 2001.
Tang et al., *Dev. Cell*, 1:227-237, 2001.
Tang et al., *Eur. J. Pharmacol.*, 15; 268(1):105-14, 1994.
Taylor et al., *J. Cell Biol.*, 142:1-11, 1998.
U.S. Pat. No. 5,399,363
U.S. Pat. No. 5,466,468
U.S. Pat. No. 5,543,158
U.S. Pat. No. 5,641,515
U.S. Pat. No. 5,846,225
U.S. Pat. No. 5,846,233
U.S. Patent Application 20020164673
U.S. Ser. No. 10/423,892
Wang et al., *Cancer Res.*, 62:1662-1668, 2002.
Wang et al., *Carcinogenesis*, 21:2293-2297, 2000.
Wataru et al., *J. Web.*, 1:1-10, 2000.
Waters et al., *J. Cell Biol.*, 141:1181-1191, 1998.
Yu et al., *Mol. Cell*, 2:581-591, 1998.

What is claimed is:

1. A method of comparing cell-cycle profiles for determining the chemosensitivity of a breast cancer cell to a taxane comprising:
   a) measuring a CDK1 activity level of a target breast cancer cell treated by a taxane in vitro, and a CDK2 activity level, a Cyclin E expression level, a p21 expression level and a CDK6 expression level of the target breast cancer cell before the target breast cancer cell is treated by the taxane in vitro, to provide a cell-cycle profile;
   b) comparing the cell-cycle profile of the target breast cancer cell with a cell-cycle profile of a breast cancer cell that is resistant to the taxane or a cell-cycle profile of a breast cancer cell that is not resistant to the taxane for determining the chemosensitivity of the target breast cancer cell to the taxane.

2. The method of claim 1, wherein the target breast cancer cell treated by the taxane in vitro is obtained from a patient.

3. The method of claim 2, wherein the target breast cancer cell treated by the taxane in vitro is a tissue sample.

4. The method of claim 3, wherein the tissue sample is biopsy tissue sample.

5. The method of claim 3, wherein the tissue sample is an ex vivo cultivated biopsy tissue sample.

6. The method of claim 3, wherein the tissue sample is a surgically dissected tissue sample.

7. The method of claim 3, wherein the tissue sample is an ex vivo cultivated surgically dissected tissue sample.

8. The method of claim 1, wherein the taxane is paclitaxel.

9. The method of claim 1, wherein the taxane is docetaxel.

10. The method of claim 2, wherein the target breast cancer cell treated by the taxane in vitro is obtained prior to administration of an anticancer therapy.

11. The method of claim 10, wherein the anticancer therapy is a chemotherapy.

12. The method of claim 10, wherein the anticancer therapy is a radiotherapy.

13. The method of claim 1, wherein the CDK1 activity level is measured using an automated analyzer.

* * * * *

UNITED STATES PATENT AND TRADEMARK OFFICE
CERTIFICATE OF CORRECTION

| | | |
|---|---|---|
| PATENT NO. | : 8,021,831 B2 | Page 1 of 1 |
| APPLICATION NO. | : 10/926409 | |
| DATED | : September 20, 2011 | |
| INVENTOR(S) | : Ueno et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 527 days.

Signed and Sealed this
Twenty-first Day of February, 2012

David J. Kappos
*Director of the United States Patent and Trademark Office*

SEQUENCE LISTING

```
<160> NUMBER OF SEQ ID NOS: 2

<210> SEQ ID NO 1
<211> LENGTH: 21
<212> TYPE: DNA
<213> ORGANISM: Artificial Sequence
<220> FEATURE:
<223> OTHER INFORMATION: Description of Artificial Sequence:  Synthetic
      Primer

<400> SEQUENCE: 1
aaacctttac tcgagtgcag a                                                    21

<210> SEQ ID NO 2
<211> LENGTH: 21
<212> TYPE: DNA
<213> ORGANISM: Artificial Sequence
<220> FEATURE:
<223> OTHER INFORMATION: Description of Artificial Sequence:  Synthetic
      Primer

<400> SEQUENCE: 2
aacaatactc ttcagcagca g                                                    21
```